US008746885B2

(12) United States Patent
Raskar et al.

(10) Patent No.: US 8,746,885 B2
(45) Date of Patent: Jun. 10, 2014

(54) METHODS AND APPARATUS FOR CATARACT DETECTION AND MEASUREMENT

(75) Inventors: Ramesh Raskar, Cambridge, MA (US); Vitor Pamplona, Porto Alegre (BR); Erick Passos, Teresina-Pi (BR); Jan Zizka, Bratislava (SK)

(73) Assignee: Massachusetts Institute of Technology, Cambridge, MA (US)

( * ) Notice: Subject to any disclaimer, the term of this patent is extended or adjusted under 35 U.S.C. 154(b) by 143 days.

(21) Appl. No.: 13/396,556

(22) Filed: Feb. 14, 2012

(65) Prior Publication Data

US 2012/0206694 A1 Aug. 16, 2012

Related U.S. Application Data

(60) Provisional application No. 61/443,199, filed on Feb. 15, 2011.

(51) Int. Cl.
*A61B 3/02* (2006.01)
*A61B 3/00* (2006.01)

(52) U.S. Cl.
USPC ............ 351/237; 351/222; 351/243; 351/246

(58) Field of Classification Search
USPC .................................. 351/237, 239, 243, 246
See application file for complete search history.

(56) References Cited

U.S. PATENT DOCUMENTS

| 6,002,484 | A  | * | 12/1999 | Rozema et al. | 356/515 |
| 6,260,970 | B1 | * | 7/2001  | Horn          | 351/246 |
| 6,905,210 | B2 | * | 6/2005  | Applegate et al. | 351/221 |
| 7,156,518 | B2 | * | 1/2007  | Cornsweet et al. | 351/246 |
| 2005/0122477 | A1 | * | 6/2005 | Alster et al. | 351/237 |
| 2009/0046248 | A1 |   | 2/2009  | Niven         |         |

OTHER PUBLICATIONS

International search report and written opinion of international searching authority, Jun. 20, 2012, PCT/US2012/025124, international filing date Feb. 14, 2012.

* cited by examiner

*Primary Examiner* — Jordan Schwartz
(74) *Attorney, Agent, or Firm* — Stephen R. Otis

(57) ABSTRACT

In exemplary implementations of this invention, cataracts in the human eye are assessed and mapped by measuring the perceptual impact of forward scattering on the foveal region. The same method can be used to measure scattering/blocking media inside lenses of a camera. Close-range anisotropic displays create collimated beams of light to scan through sub-apertures, scattering light as it strikes a cataract. User feedback is accepted and analyzed, to generate maps for opacity, attenuation, contrast and sub-aperture point-spread functions (PSFs). Optionally, the PSF data is used to reconstruct the individual's cataract-affected view.

20 Claims, 20 Drawing Sheets

BACK
SCATTERING

FORWARD
SCATTERING

SAMPLED SUB-APERTURES

SUB-APERTURES PSFs

COMBINED DEPTH-PSFs

METHODS AND APPARATUS FOR CATARACT DETECTION AND MEASUREMENT

RELATED APPLICATIONS

This application claims the benefit of U.S. Provisional Application Ser. No. 61/443,199, filed Feb. 15, 2011, the entire disclosure of which is herein incorporated by reference.

FIELD OF THE TECHNOLOGY

The present invention relates generally to instruments for detection and measurement of cataracts.

SUMMARY

A cataract-affected eye forward-scatters light before it reaches the retina, due to a fogging or clouding of the crystalline lens.

In exemplary implementations of this invention, this forward scattering is measured in order to compute quantitative maps for opacity, attenuation, contrast, and point-spread function (PSF) of cataracts.

In exemplary implementations, an optical system is placed close to the viewer's eye, and projects time dependent images onto the fovea. The optical system creates collimated beams of light to scan the crystalline lens. The path traveled by these beams varies over time, passing through different sectors of the crystalline lens at different times. These beams forward scatter when the light path hits a cataract, which alters the image seen by the viewer. An input device accepts input (feedback) from the viewer, regarding the images perceived by viewer. A processor computes maps for opacity, attenuation, contrast, and point-spread function (PSF) of cataracts. The computations are based, at least in part, on data regarding the viewer input, and on data regarding variations in the light path. A viewer may use this invention to assess his or her own cataracts. Optionally, the processor uses the PSF data to reconstruct the viewer's cataract-affected view.

The optical system may comprise, for example: (a) dual-stacked LCDs and a lens, (b) a projector, diffuser, pinhole mask and lens, (c) a cellphone screen, pinhole mask and lens, or (d) another portable high-contrast light-field display.

It is helpful to contrast this invention to conventional diagnostic tools. Conventional devices for assessing cataracts (e.g., a slit-lamp) rely on back-scattering of light, whereas this invention measures forward scattering. Conventional tools require specialized training, whereas (in exemplary implementations), this invention does not.

The above description of the present invention is just a summary. It is intended only to give a general introduction to some illustrative implementations of this invention. It does not describe all of the details of this invention. This invention may be implemented in many other ways.

BRIEF DESCRIPTION OF THE DRAWINGS

In FIG. 8A, the optical system includes dual-stacked LCDs and a lens.

In FIG. 8B, the optical system includes a DLP projector, diffuser, mask and lens.

In FIG. 8C, the optical system includes a cellphone, mask and lens.

The above Figures illustrate some illustrative implementations of this invention, or provide information that relates to those implementations. However, this invention may be implemented in many other ways. The above Figures do not show all of the details of this invention.

DETAILED DESCRIPTION

In exemplary implementations of this invention, a light-field display projects time-dependent patterns onto the fovea. To create attenuation and point spread function maps, a viewer matches patterns that have passed, alternately, through scattering and clear regions of the crystalline lens. Interactive software measures the attenuation and point-spread function across sub-apertures of the eye. Size, position, density, and scattering profile of cataracts are then estimated.

Figure 1A:
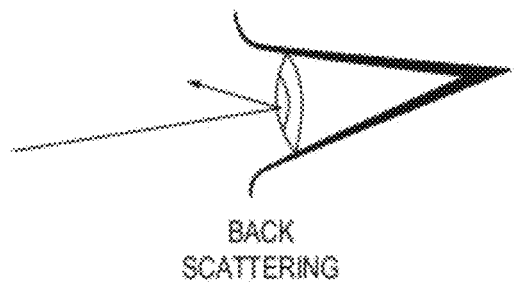
FIG. 1A shows back scattering of light in a human eye.
Figure 1B:
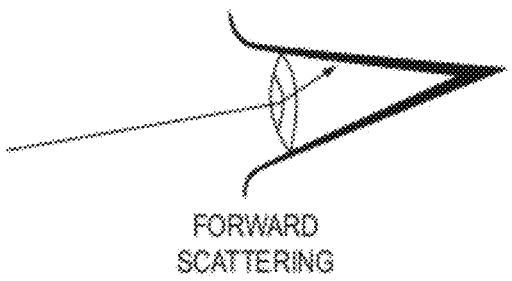
FIG. 1B shows forward scattering of light in a human eye.

FIGS. 1A and 1B are diagrams that illustrate back-scattering of light and forward-scattering of light, respectively. Conventional techniques for detecting cataracts rely on back scattering measurements. Instead, in illustrative embodiments, this invention relies on forward scattering towards the retina.

Figure 2A:
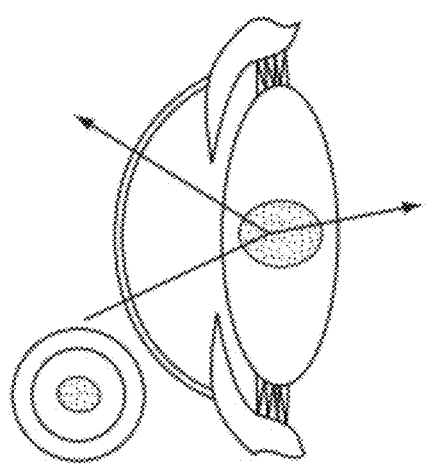
FIGS. 2A, 2B, and 2C show examples of nuclear, sub-capsular and cortical cataracts, respectively.
Figure 2B:
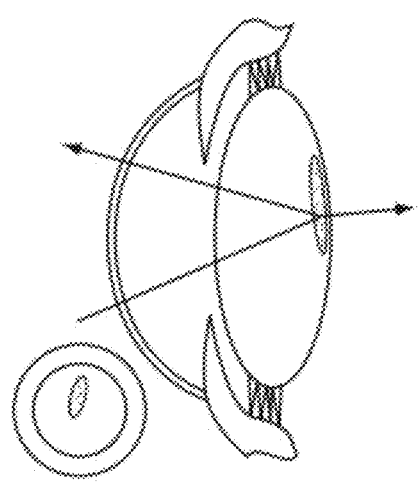
Figure 2C:
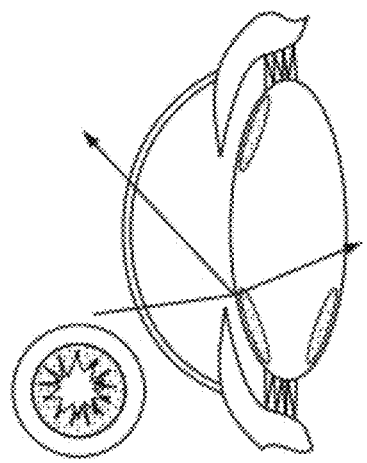

FIGS. 2A, 2B and 2C are diagrams that show common types of cataracts. A nuclear cataract (FIG. 2A) forms on the center of the crystallin, grows towards the periphery, and is strongly related to the aging process. A sub-capsular cataract (FIG. 2B) starts on the back of the crystallin, and is often due to diabetes. A cortical cataract (FIG. 2C) starts on the periphery, and grows inwards to its center. These cataracts alter vision due to back scattering and forward scattering. Back scattering reduces the visual acuity by partially blocking light. Forward scattering blurs the retinal image, decreasing contrast. Pupil size determines the strength of the effects. FIGS. 2A, 2B, and 2C show examples of nuclear, sub-capsular and cortical cataracts, respectively.

Figure 3A:
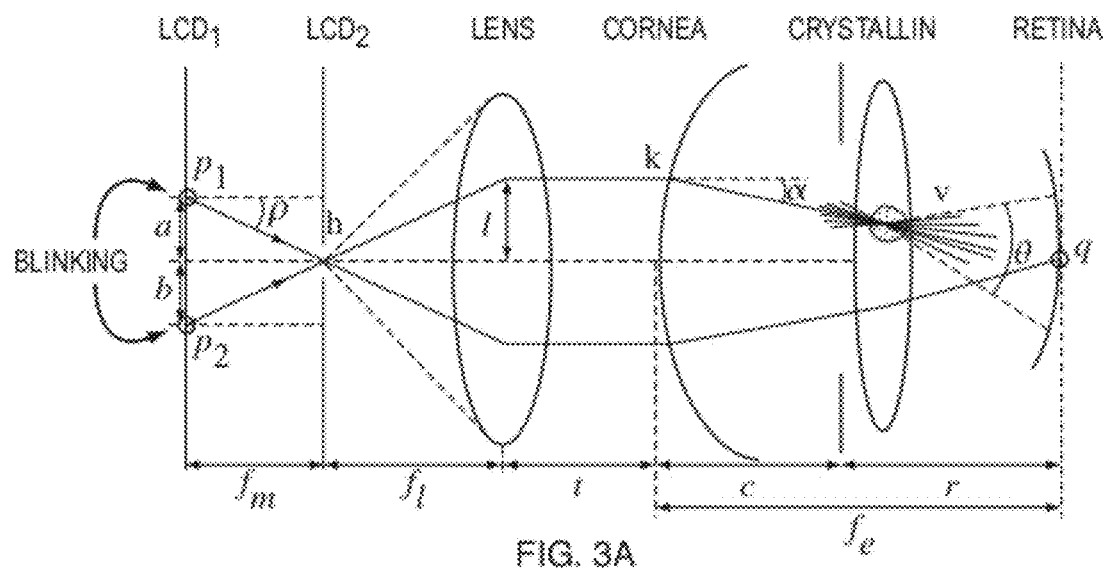
FIG. 3A is a diagram that illustrates an approach for detecting the location of cataracts in a human eye.
Figure 3B:
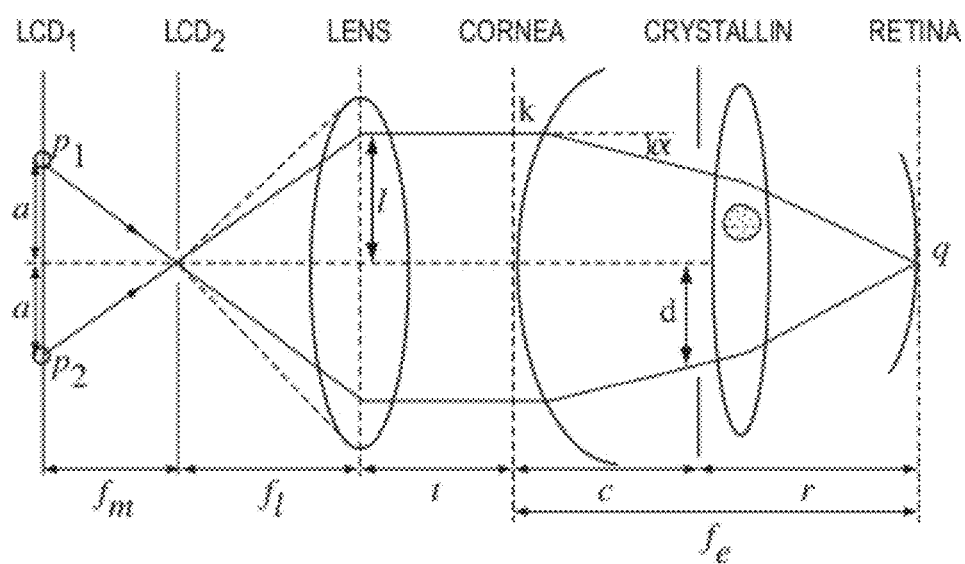
FIG. 3B is a diagram that illustrates an approach for measuring pupil size.
Figure 3C:
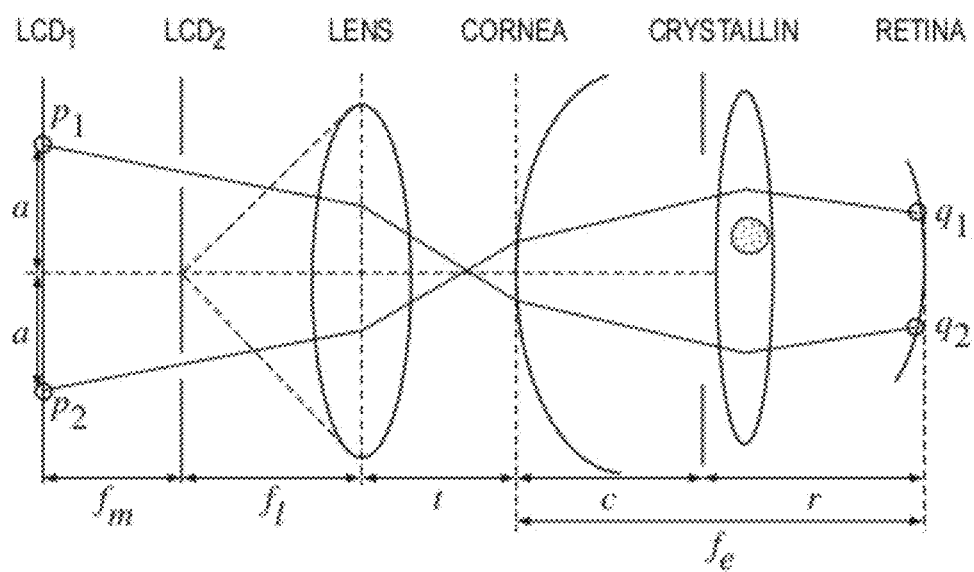
FIG. 3C is a diagram that shows reference points being projected onto the retina.

In exemplary implementations, a time-dependent gaze-controlling scanning mechanism is used to assess parameters of the human eye. FIG. 3A shows a diagram of the setup in flat-land and FIGS. 3B and 3C show two applications.

As shown in FIG. 3A, two stacked LCD and a lens create collimated beams of light. The LCDs function as a programmable anisotropic display that can produce directed light rays. An additional lens in front of the display increases light efficiency, reduces diffraction, and collimates the light beams. These collimated beams converge to the same point on the retina. The optical apparatus is positioned very close to the subject's cornea and its components are aligned with each other.

As shown in FIG. 3A: Each pixel on $LCD_1$ maps to a region on the crystallin and each pixel on $LCD_2$ corresponds to a retinal position. Patterns drawn on $LCD_2$ are reflected on the retina, while the brightness of all pixels on $LCD_1$ are integrated on the same retinal point. A central pinhole in $LCD_2$ traces rays to the center of the fovea. Positions $p_i$ inside the crystallin are a function of the angle $\rho$:

$$v(\rho) = f_l \tan \rho - c \tan \alpha \quad (1)$$

where the bending angle $\alpha$ is defined by the optical corneal power in the point k.

To create patterns on the subject's view, the pinhole on $LCD_2$ changes to the desired pattern. The position h on $LCD_2$ is mapped to the retina as (derived from compound lens equation):

$$q(h) = \frac{(-f_e^2 - f_e f_l)h}{f_l(-f_e - f_l + f_e t)} \quad (2)$$

The setup shown in FIG. 3A traces light from each $p_i$ through many regions of the crystallin, one at a time. Each beam propagates the effect of possible occluders and imperfections to the central point of the fovea. The displayed image disappears on a mostly reflective cataract spot and scatters when the ray finds a semi-transmissive spot. An input device accepts input from the viewer, which input is indicative of when the displayed image disappears.

If a single pinhole is displayed by $LCD_2$ (as shown in FIG. 3A), all bright pixels on $LCD_1$ will focus at the same spot q on the retina. Thus $LCD_1$ defines the brightness of each retinal point, while $LCD_2$ controls the position and shape of q.

FIG. 3B shows how pupil size is measured, in exemplary implementations of this invention: Subject chooses the biggest possible angle "a" while still seeing q.

FIG. 3C illustrates the use of reference points used to control eye movement and gaze, in exemplary implementations of this invention. The lens is positioned at one focal length ($f_l$) from the display. The distance $f_m$ defines the angular resolution.

In the examples shown in FIGS. 3A, 3B and 3B, a near-Lambertian light source is placed behind $LCD_1$.

Figure 4:
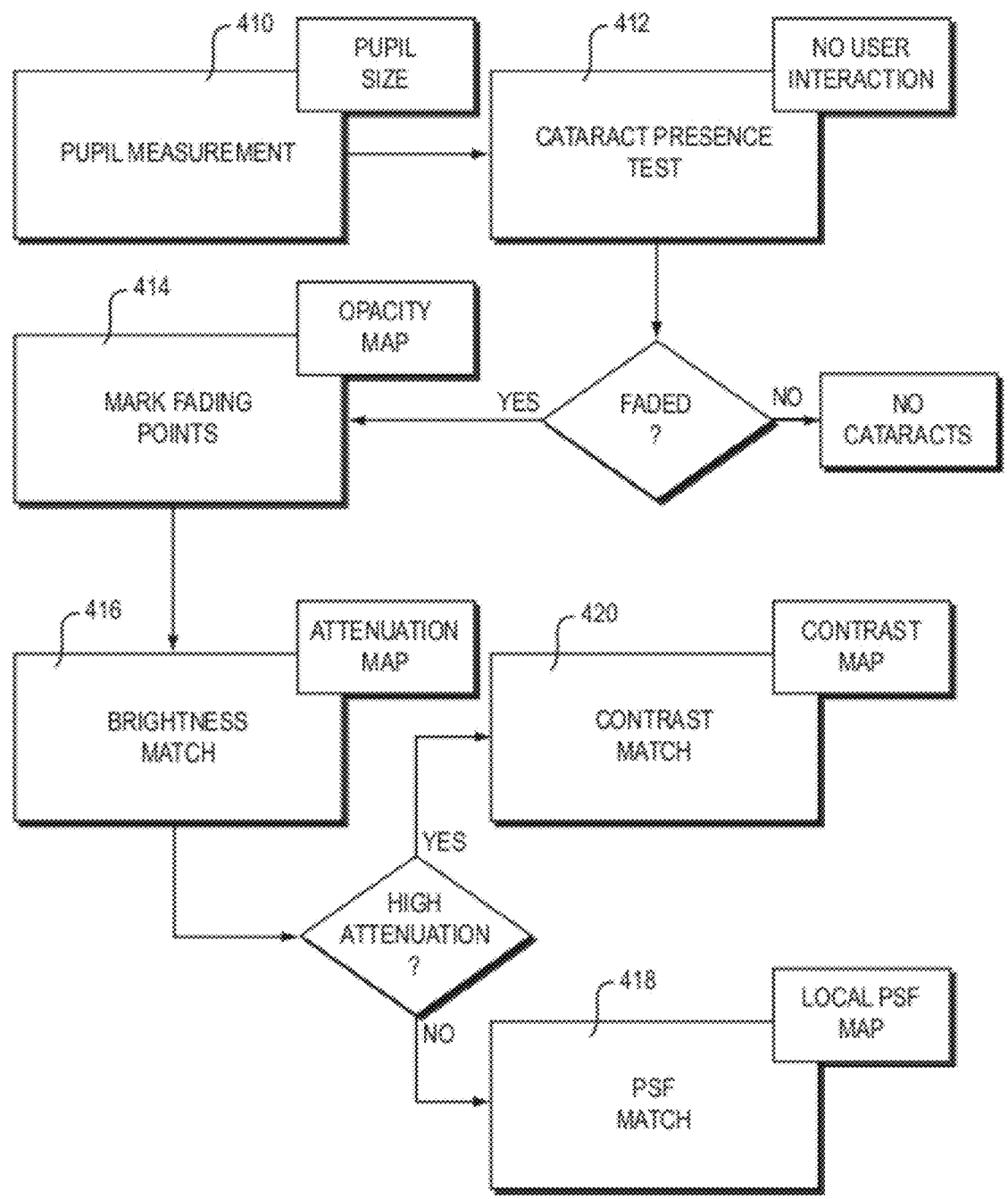
FIG. 4 is a high-level flow chart for measuring cataracts.

FIG. 4 is a flow chart that shows an interactive method to measure cataracts, in an exemplary implementation of this invention. After measuring the pupil size, which defines the discretization of the pupil area and enables the computation of the cataract size in meaningful physical units, the subject's crystallin is sequentially scanned to identify the presence of cataracts. If cataracts are found, the subject marks the position of opacities and, in a later step, measures the light attenuation for each affected sub-aperture of the eye. The measured attenuation values estimate the intensity of the sub-aperture PSF peak. The subject then performs perceptual pattern matching to measure the tail of the PSF. If the light attenuation is big, the tail may be bigger than the fovea, and its direct measurement is not reliable. In that case, contrast-sensitivity tests are used to approximate the PSF.

In the example shown in FIG. 4, the method involves six steps:

The first step 410 is pupil measurement. This step is illustrated in more detail in FIG. 3B, which shows a simplified ray diagram to measure pupil size with two light beams in flat-land. In practice, a circle with radius a of dots $p_i$ is displayed on $LCD_1$, and a dot (pinhole) is displayed on the center of $LCD_2$. Parallel rays enter the eye and converge to a single point q on the fovea. Via interactive software, the subject increases a up to a point where the light rays are blocked by the iris and the projected pattern disappears. The pupil radius is given by $d(a) = a - c \tan \alpha$, where c is the anterior chamber depth. A circular pupil is assumed, thus the search is 1D.

The second step 412 is a cataract presence test. In this second step 412, the lens is rapidly scanned to check for the presence of cataracts. At the end of this rapid scan, the user provides input (to an input device) regarding whether the user saw any blinking or fading of the light. If the user indicates that the user saw blinking or fading of the light during the rapid scan, this indicates that there is at least one cataract. If the user indicates that the user did not see any blinking or fading, this indicates that there is no cataract. The rapid scan involves "no interaction", in the sense that the user does not press keys during the scan, but rather waits until the end of the scan to provide input. Based on this rapid scan, it can be determined whether there are any cataracts, but not where they are located. This rapid scan is performed as follows: Testing regions (which are subdivisions of the crystallin) are selected, according to the pixel density of the LCD stack, Equation 1, and pupil size. A single dot $p_1$ is displayed on $LCD_1$ and a pinhole is opened on $LCD_2$. Each move of $p_1$ scans a different region on the crystallin. In this scanning, $p_1$ is continuously changing position to cover the visible crystallin. The apparent sudden blinking or fading of the viewed pattern (e.g., case of $p_2$ in FIG. 3A) reveals the presence of cataracts.

The third step 414 is to mark fading points, for an opacity map. If any scattering spot is found in second step 412, then, in a third step 414, the scanning procedure is repeated more slowly with the subject's feedback. In this slower scan, software slows the frequency of changes in $p_1$ and allows the subject to mark faded regions by pressing keys. Since the subject does not see the pattern moving, audio feedbacks (beeps) indicate every change in $p_1$.

The subject presses keys during this slower scan to indicate when the subject sees the image suddenly fade or blink (which occurs when the light path intersects a cataract).

Based on data gathered in this step, an opacity map is created, that indicates the location of the cataracts in the eye (but not how much they attenuate light). The opacity map concatenates the binary visibility functions for each sub-aperture The fourth step 416 is a brightness match, for an attenuation map. The attenuation map measures the relative light attenuation across the crystallin. $LCD_1$ shows a pair of alternating dots (see FIG. 3A). $p_1$ is computed as the farthest point on the opacity map from the cataract spots. $p_2$ is a marked spot on the opacity map. Since both are projected on q at different time-slices, the subject sees similar patterns with oscillating brightness. The subject decreases the intensity level of the clear-path light beam and thus brighter $p_1$ until the oscillation stops. This same task is executed for all marked regions on the opacity map. In the end, the attenuation map is built, showing the relative density of the cataracts (i.e., how much they attenuate light).

In this fourth step 416, the relative density of the cataracts (how much they attenuate light) is determined by presenting two alternating paths of light that focus to the same point on the retina. One of the paths is through a clear region of the eye and the other through a scattering region (cataract). The intensity of the light through the clear region is reduced, until it matches the intensity of light through the scattering region. Based on data gathered in this stage, an attenuation map is created.

A fifth step is point-spread function matching 418: Similar to the brightness match, subject compares and matches alternating patterns $p_i$ on $LCD_1$. Two patterns are drawn on $LCD_2$, one for each $p_i$. The former is a single pixel stimulus that hits the cataract spreading light onto the retina. The latter is a linear combination of a Gaussian and a box functions, which describes a sub-aperture PSF:

$$c(x)=\beta g(\sigma,x)+(1-\beta)p(x) \quad (3)$$

where $\beta$ is a scaling factor defined by the measured attenuation value, g is a normalized Gaussian function, $\sigma$ is the standard deviation of the Gaussian function, and p is a normalized box function. In the absence of blur, $\beta=0$. For each marked spot on the opacity map, the subject changes the values of $\sigma$ to best match the visualized PSF. In this fifth step 418, for a low scattering spot, sub-aperture PSF matching is performed. The peak and Gaussian spread are measured for each scattering spot. Based on data gathered in this stage, a PSF map is created. The PSF matching is well suited for low attenuation scattering spots.

A sixth step is a contrast-sensitivity test 420: This test is well suited for a high scattering spot. In this case the subject increases the contrast of a displayed pattern up to a point where the displayed pattern becomes discernible. Based on data gathered in this stage, a contrast map is created. This contrast-sensitivity is a replacement for the PSF measurement procedure. Wider PSFs project their tail out of the fovea and thus the subject may not be able to reliably measure it. In the contrast-sensitivity test, for each attenuated sub-aperture, a single $p_i$ is rendered on $LCD_1$ and a low-contrast 3 pixel-wide randomly-rotated letter C on $LCD_2$. In the beginning, user sees a white square. The subject increases the contrast until C becomes visible. The rotation degree (0, 90, 180 or 270) of C is marked and noted. This visual acuity test is repeated for each marked sub-aperture, generating a complete map in the end. Alternately, a pattern other than the letter C may be used.

In exemplary implementations of this invention, because all collimated beams are projected onto the fovea, no matter from which part of the cornea they enter the eye, the subject tends to keep looking to the same point and not to gaze in other directions. However, the subject can shift the direction of gaze by the width of the pupil diameter, and remain seeing the same image. In order to prevent this, and keep the user's gaze in the same place, reference points are opened as a circular arrangement of patterns on $LCD_2$, as shown in FIG. 3B. Part of the circle disappears when the subject moves beyond a certain limit. With this technique, the subject can detect when the gaze is off center, and then return to the original position.

In exemplary implementations, the system resolution is as follows: Assuming h (in FIG. 3A) is a pinhole, the size of the cross section defined by the collimated light beams between the lens and the cornea is given by $s(p)f_l/f_m$, where $s(p)$ is the radius of the pattern p on $LCD_1$. Thus the bigger $f_m$, the smaller the beam radius is. The sampling resolution on the crystallin is defined by the discretization of the angle ρ (Equation 1), which is dependent on the pixel size on both $LCD_1$ and $LCD_2$. The retinal resolution is defined by pixel pitch on $LCD_2$ (Equation 2). To match the fovea (radius of ≈0.92 mm), light rays have to reach the cornea at maximum angle of ρ=2.12°. Thus the biggest reliable pattern on $LCD_2$ has the radius of $f_l \tan(\rho)$.

The additional lens on top of $LCD_2$ in FIG. 3A plays an important role in handling accommodation. Subjects can focus on the image displayed by $LCD_2$ just like any other object seen through a lens. The lens tends to force the eye to focus on the pinhole or the pattern drawn on $LCD_2$. The lens is located one focal length away from $LCD_2$.

In exemplary implementations of this invention, cataract maps are used by a processor to render (reconstruct and simulate) an individual's cataract-affected view. The resulting view can be shown to the subject, to make the subject aware of his condition by showing images of how his vision is currently deformed and how it will be after a cataract surgery. Or it can be shown to a person other than the subject, so that the other person can see what the scene looks like through the cataract-affected eye of the subject.

In exemplary implementations, scenes of daily activities are taken using a standard camera, such as someone driving at night, low contrast features and so on. They are displayed in a standard monitor. An algorithm uses the captured cataract maps to convert the displayed picture into the view of an affected individual. The input picture is also displayed on the monitor to establish a benchmark. Two different persons (e.g., a cataract-affected patient and a doctor) can both see the effect the cataract is causing in the patient's vision. Since the patient is observing images from a monitor and not the real scenes, the cataracts do not affect the patient's view of the monitor to the same extent as they affect the patient's view of the real scene. Renderings allow a patient and doctor to share a visual experience, facilitating dialogue and diagnosis. A comparison of the rendering (which approximates the cataract-affected view) and a normal view can be used to help patients decide when to take the surgery, to help the doctor understand a given patient's condition, and in teaching ophthalmology.

In exemplary implementations, the vision of a specific individual affected by cataracts can be simulated (rendered). The procedure depends on what maps are provided as input. If only an opacity map (which says how much of the aperture is blocked by a cataract) is given as input, aperture structure is transformed into the eye's point spread function, using well-known algorithms. If attenuation or contrast maps are given as input, they are converted into point spread function maps and then the procedure for converting PSF maps to a cataract-affected view (described below) can be applied. Attenuation and contrast values are measured per sub-aperture, like point spread function maps. The PSF for each sub-aperture is a 2D gaussian-like profile (Equation 3) where sigma is the contrast value and the gaussian maximum intensity is the attenuation value.

If a point spread function (PSF) map is given as input, then a clear picture can be transformed into a cataract affected one (which simulates the vision of a specific individual affected by cataracts), as follows:

An accommodation-dependent convolution of sub-aperture PSFs simulates the view of a cataract-affected eye. Depth-masked patches of the input image are convolved with their corresponding depth-dependent PSFs. The results are combined into the final image. Each depth-dependent PSF is computed by combining the measured sub-aperture PSFs. FIG. 6D illustrates how the combined PSF changes with accommodation. At the focal plane, all sub-aperture PSFs are just superposed and added, averaging their values. At depths away from the focal plane, the sub-aperture PSFs are shifted from the center according to the distance to the focal plane and the aperture, given by the pupil diameter. Computation of these depth-dependent PSFs can be defined by a sum over all sub-apertures.

$$PSF(B) = \sum_i PSF_i + B\vec{g}_i \quad (4)$$

where B is a depth-offset in diopters (reciprocal of the distance in meters $B=1/d_m$) from the plane of focus defined by the accommodation, $\vec{g}_i$ is the vector that represents the shift of a given sub-aperture i from the center of the lens, and $PSF_i$ is i's PSF. The product $B\vec{g}_i$ models how the circle of confusion projected through i gets shifted from the center of the image as a function of depth.

The final image is given by the sum of the depth-masked patches convolved with their respective PSFs for all depths in the scene:

$$IMG(A) = \Sigma h(A,B) \otimes PSF(B) \quad (5)$$

where h(A,B) gives the depth-masked patch of the input image I for accommodation A in diopters and is defined pixel-wise by:

$$h_{x,y}(A, B) = \begin{cases} I_{x,y} & \text{if depth}(x, y) = A + B \\ 0 & \text{otherwise} \end{cases} \quad (6)$$

where $I_{x,y}$ is the intensity of the pixel x,y, and depth is the distance from camera to the projected point x,y in diopters.

Depth information is captured with a Z-camera, i.e., a camera in which each pixel stores the distance from the object to the camera instead of its color. Microsoft® Kinect® is an example of such technology.

Figure 5A:
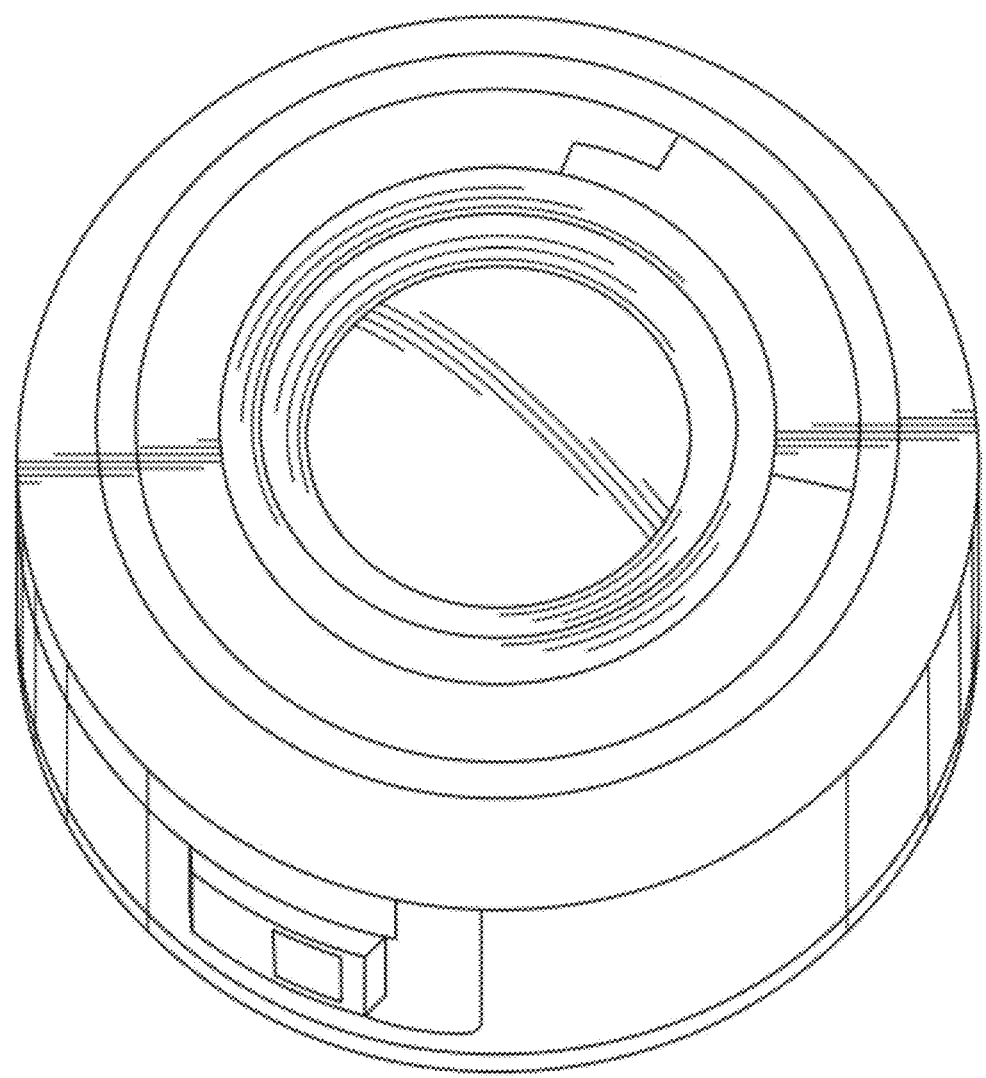
FIG. 5A shows a "cataract-affected" camera. An 80 degree diffuser (not shown) has been inserted behind a 55 mm lens of an SLR camera, to simulate a cataract.
Figure 5B:
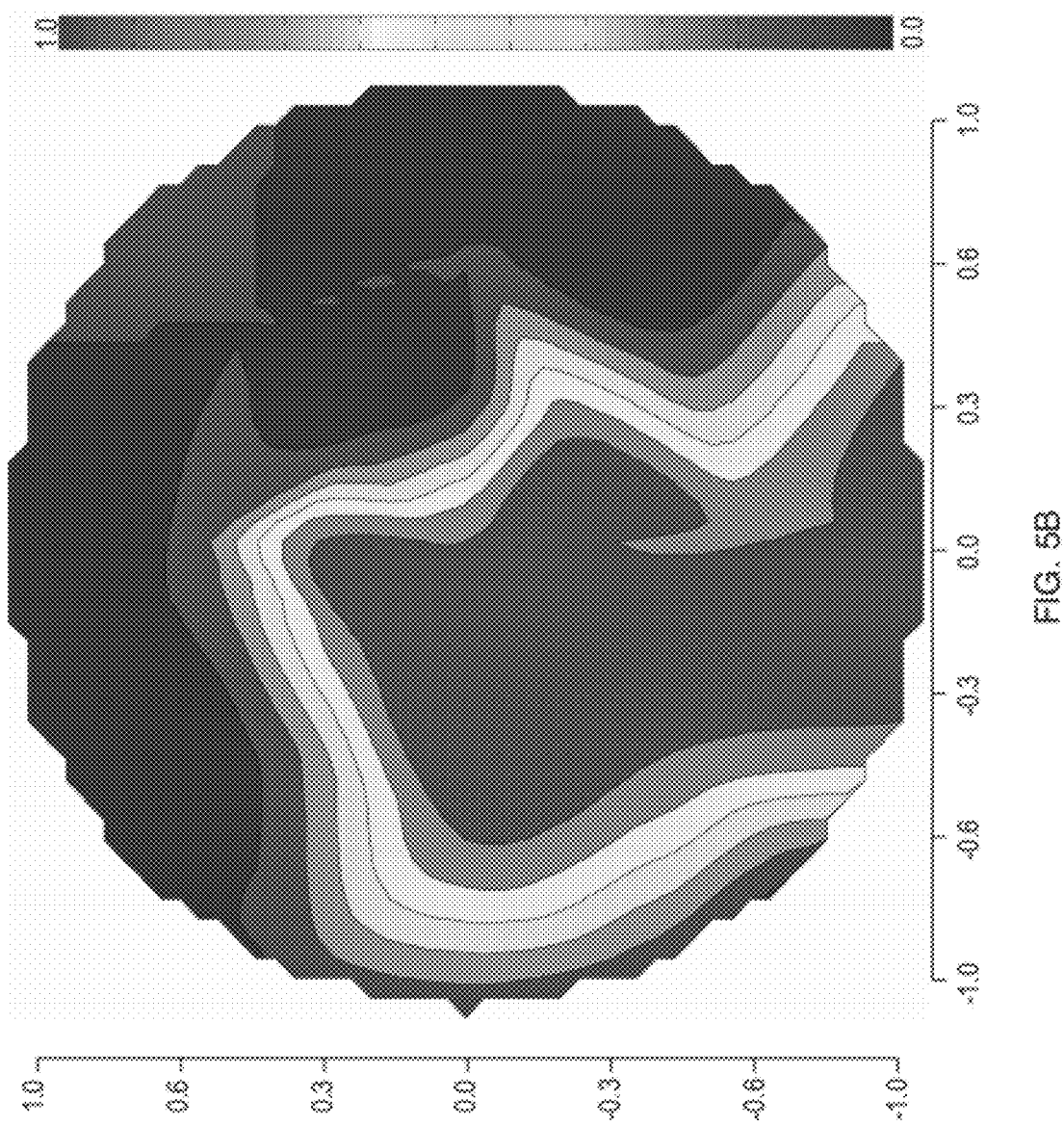
FIG. 5B shows an attenuation map for the cataract-affected camera.
Figure 5C:
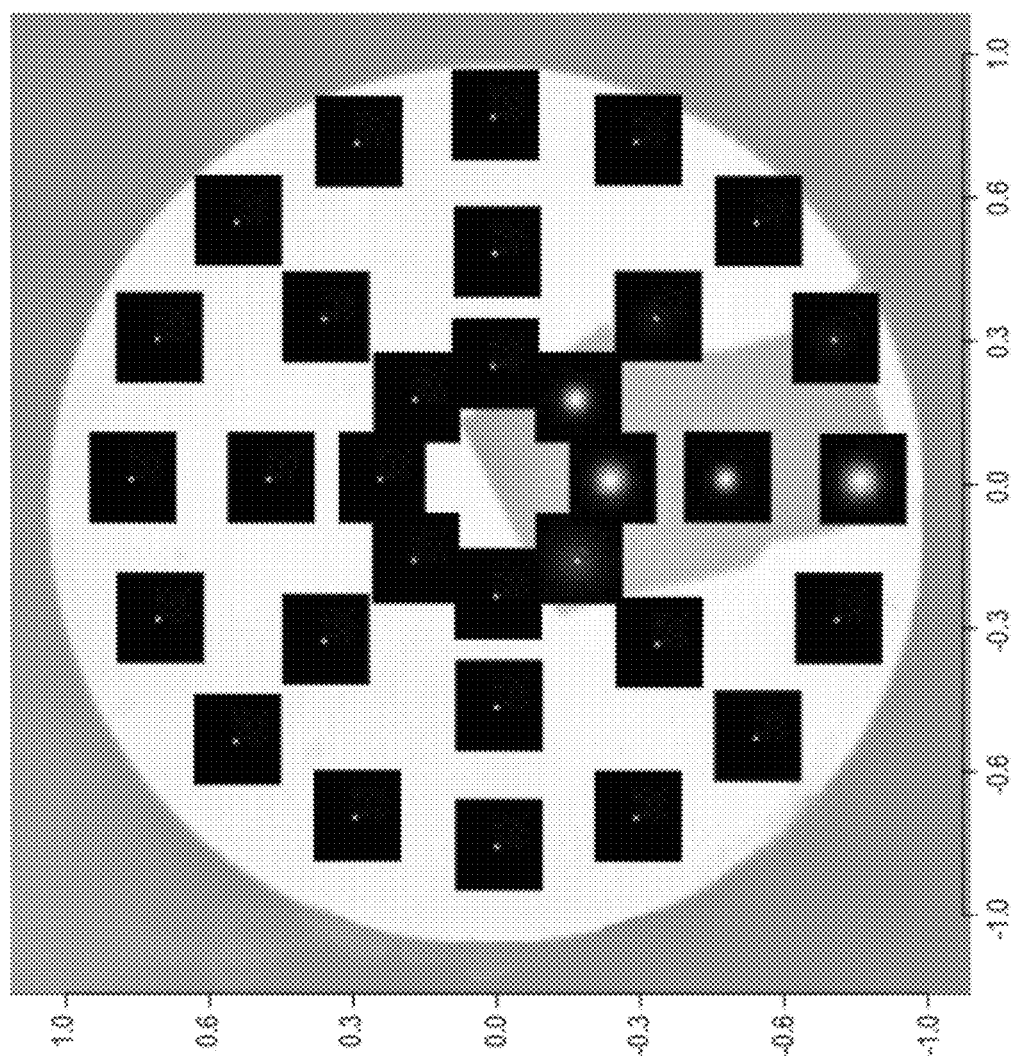
FIG. 5C shows the measured sub-aperture PSFs for the cataract-affected camera.
Figure 5D:
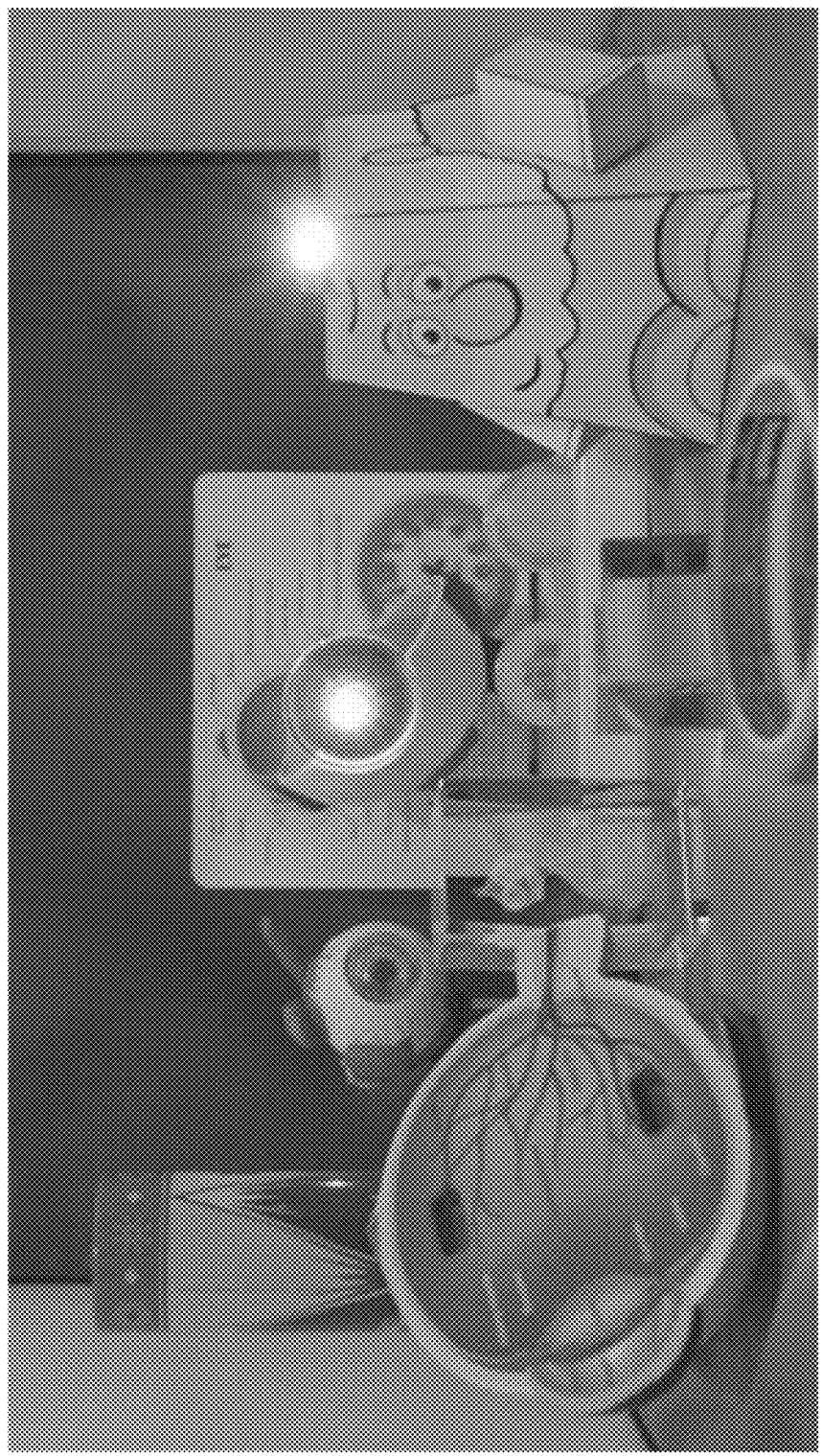
FIG. 5D is a photograph of a scene, taken by the SLR camera, but without the diffuser (i.e., it shows a normal view, without a simulated cataract).
Figure 5E:
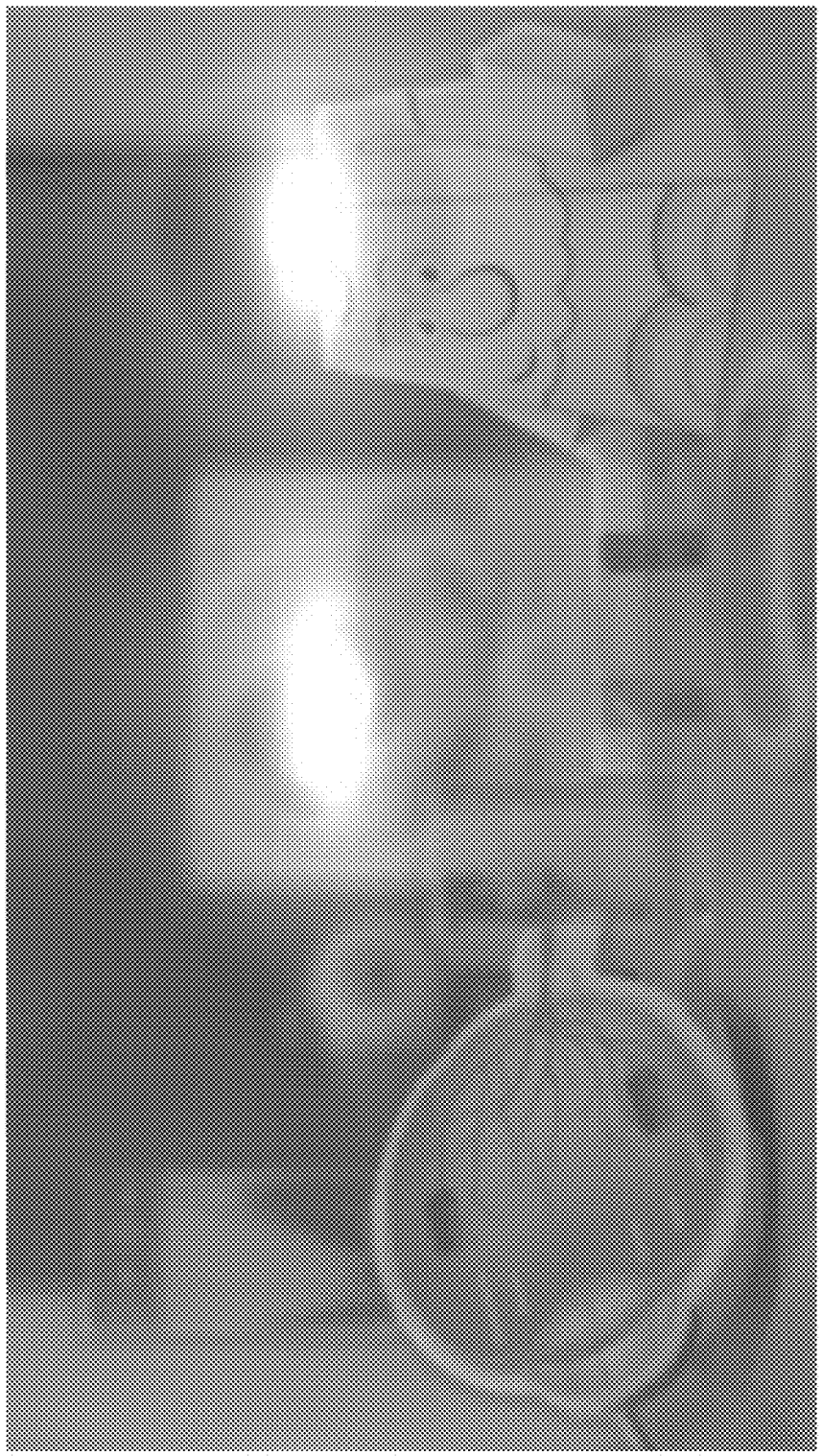
FIG. 5E shows a rendering of a cataract-affected view. The rendering is intended to approximate the same scene (that is the subject of the FIG. 5D), as it would be seen by the cataract-affected camera. The rendering is produced by, among other things, convolving the "normal" view with subaperture PSFs.
Figure 5F:
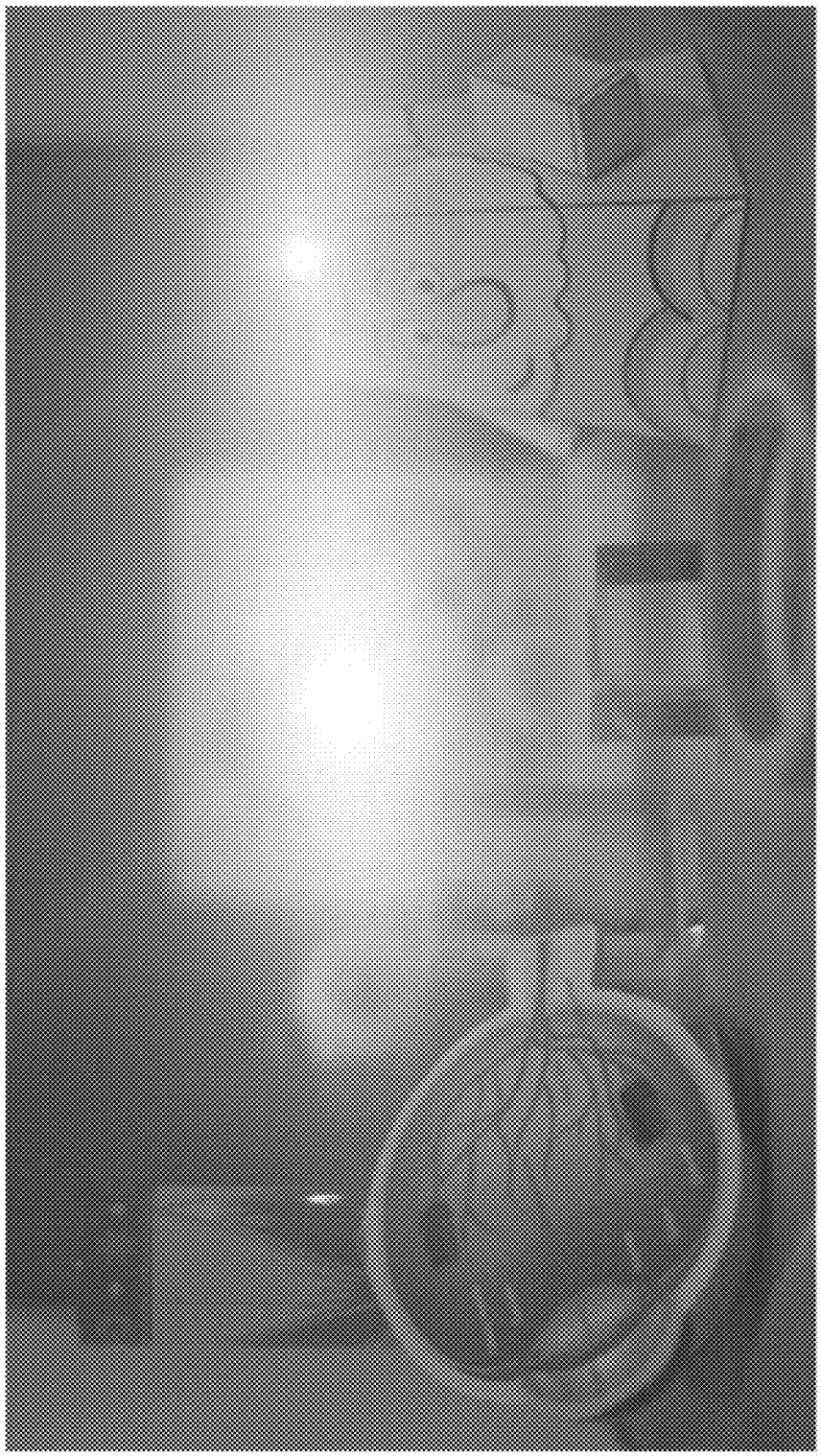
FIG. 5F shows a photograph of the scene, as actually taken by the cataract-affected camera.

Given sub-aperture PSFs, this depth-based approach renders artifacts which are similar to those described by cataracts-affected subjects, also computing the expected depth-of-field (see FIGS. 5E and 5F).

Optionally, an augmented version of the Ritschel glare model is added to the computed PSF, in order to account for diffraction from the pupil, to simulate glare, halos and other effects created by a non-clear aperture, and to account for lens fibers effects and reduced light intensity reaching the retina due to cataract opacities. The attenuation map is added as an extra multiplication step to the Ritschel glare model so that the light going through parts of the eye lens is attenuated as measured. (The Ritschel glare model is described in RITSCHEL, IHRKE, M., FRISVAD, J. R., COPPENS, J., MYSZKOWSKI, K., & SEIDEL, H., 2009, Temporal glare: Real-time dynamic simulation of scattering in the human eye. Comp. Graph. Forum 28, 2, 183-192).

FIG. 5A shows a "cataract-affected" camera. An 80 degree diffuser (not shown) has been inserted behind a 55 mm lens of an SLR camera, to simulate a cataract. FIG. 5B shows an attenuation map for the cataract-affected camera. FIG. 5C shows the measured sub-aperture PSFs for the cataract-affected camera. FIG. 5D is a photograph of a scene, taken by the SLR camera, but without the diffuser (i.e., it shows a normal view, without a cataract). FIG. 5E shows a rendering of a cataract-affected view. The rendering is intended to approximate the same scene, as it would be seen by the cataract-affected camera. The rendering is produced by, among other things, convolving the "normal" view with sub-aperture PSFs. FIG. 5F shows a photograph of the scene, as actually taken by the cataract-affected camera. Note the similarity between FIG. 5E (simulation of scene as seen by cataract affected camera) and FIG. 5F (actual scene as seen by the cataract affected camera).

Figure 6A:
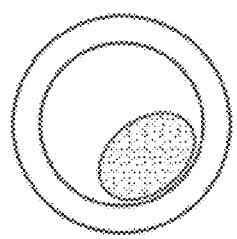
FIG. 6A is a diagram showing a front view of a cataract-affected eye.
Figure 6B:
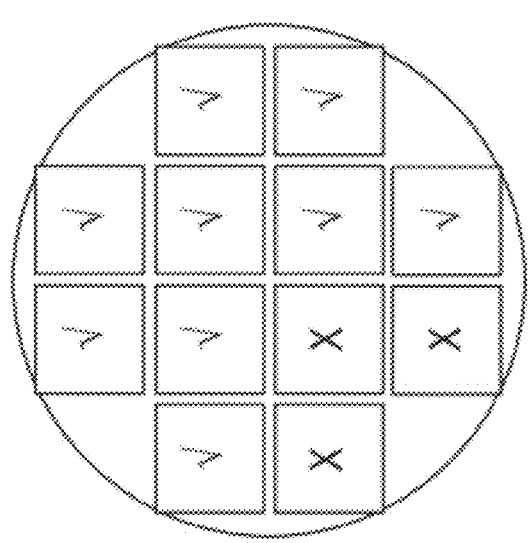
FIG. 6B is an opacity map that shows which sampled sub-apertures are scattering regions.
Figure 6C:
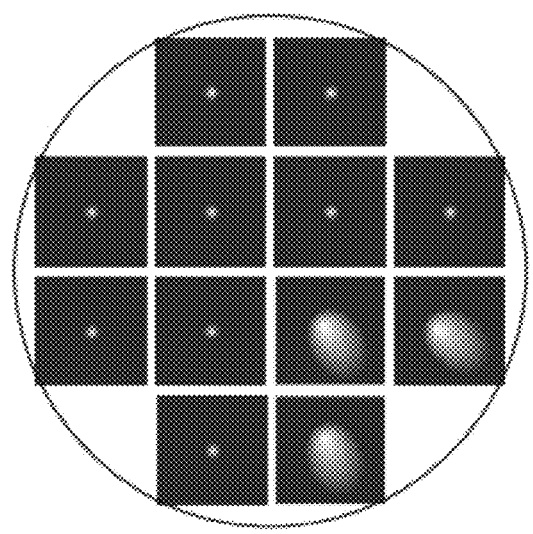
FIG. 6C shows sub-aperture PSFs.
Figure 6D:
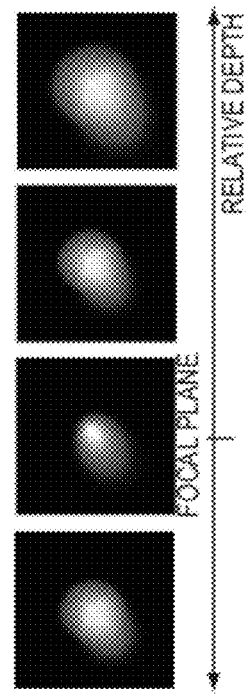
FIG. 6D shows combined depth PSFs.

FIG. 6A is a diagram showing a front view of a cataract-affected eye. FIG. 6B is an opacity map that shows which sampled sub-apertures are scattering regions. On the opacity map, check marks represent good light paths and Xs represent scattering regions reported by the subject. FIG. 6C shows sub-aperture PSFs. FIG. 6D shows combined depth PSFs.

Figure 7:
FIG. 7 shows a rendered scene that approximates how the scene would appear to a cataract-affected visual system.

FIG. 7 shows a rendered scene that approximates how the scene would appear to a cataract-affected visual system.

Figure 8A:
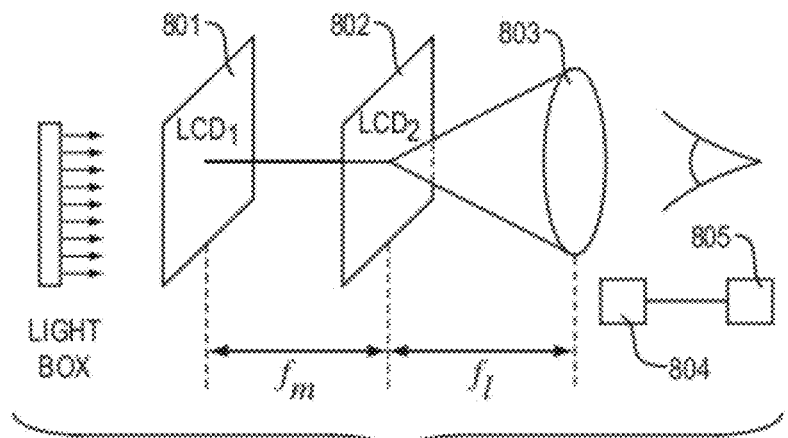
FIGS. 8A, 8B and 8C are diagrams, each of which shows a different optical system for delivering light to an eye.
Figure 8B:
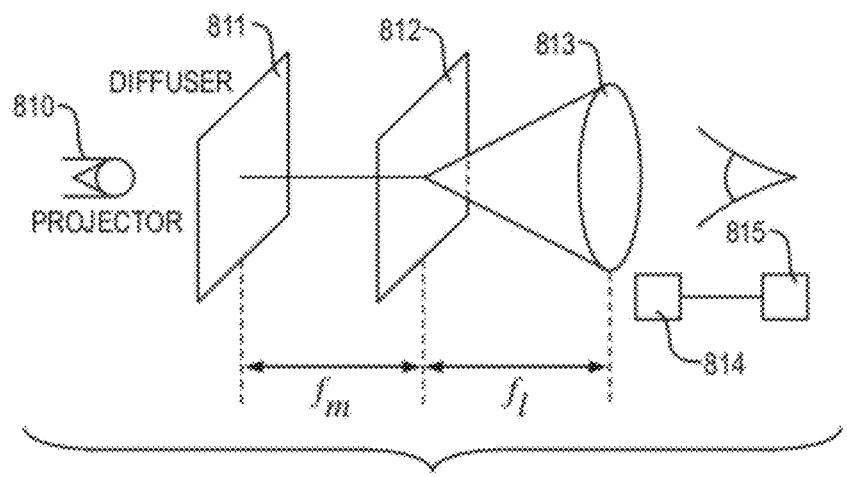
Figure 8C:
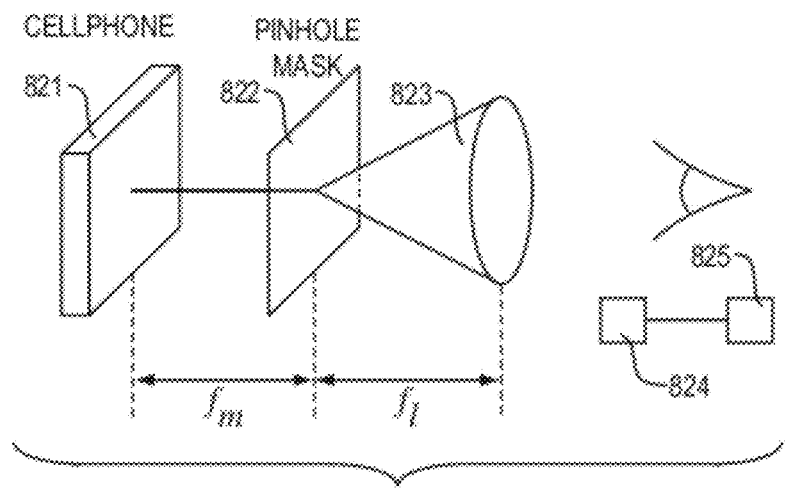

FIGS. 8A, 8B and 8C are diagrams of optical systems used in three different prototypes, respectively, of this invention.

In a first prototype (shown in FIG. 8A), the optical system includes a dual-LCD monitor built using two 18" LCD TFT monochrome medical LCD monitors 801, 802 stacked $f_m=24$ mm apart, with brightness of 700 cd/m², contrast ratio of 550:1, 90 DPI (280 μm pixel pitch) and a 20-diopter lens 803, 50 mm from the stack. (FIG. 8(a)). A single-pixel pattern is used on $LCD_1$ which reaches a scanning resolution of 510 μm on the crystallin. Since these LCD panels do not have color filters, the aberrations are smaller than traditional monitors and the high static contrast gives a smaller residual light level for black pixels.

Since $LCD_2$ does not change for attenuation and opacity maps, by replacing it for a printed pinhole mask, a cheaper version of the same optics can be achieved, which is still capable of measuring the opacity and attenuation maps, but cannot measure the contrast map or point-spread functions. This setup can be implemented as a clip-on for any high-contrast spatial light modulator. This approach was used in a second prototype (shown in FIG. 8B). In the second prototype, the optical system includes a DLP Projector comprising a Mitsubishi PK10 pocket projector (DMD) 810 and a 50×40 mm diffuser 811 as projection screen, at 800×600 in pixel resolution reaching 62 μm in pixel pitch. A pinhole mask 812 (pinhole radius of 100 μm is placed 60 mm away from the screen, a 16-diopter lens 813 is 62 mm away from the mask. This setup uses a single-pixel pattern and has a scanning resolution of 56 μm on the crystallin.

In a third prototype (shown in FIG. 8C), the optical system includes a cell phone. The cell phone setup uses a Samsung® Behold II (180 DPI or 141 μm on pixel pitch) 821, with a static pinhole mask 822 (pinhole radius of 100 μm) placed 40 mm from the display, and a 25-diopter lens 823 placed 40 mm from the mask. Using a 3×3-pixels pattern on $LCD_1$, the scanning resolution is 370 μm on the crystallin.

Figure 8D:
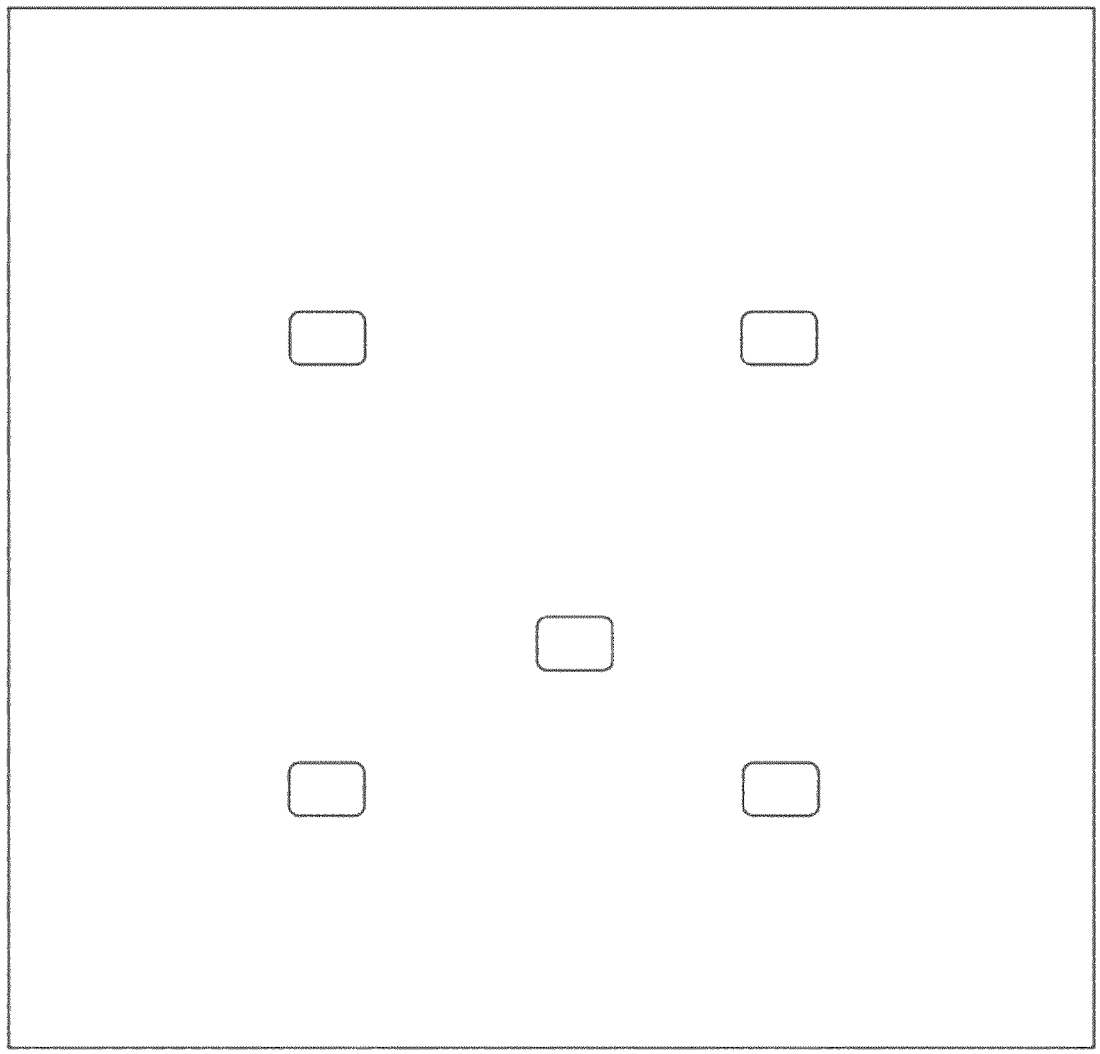
FIG. 8D shows a display on a cellphone screen, in a cellphone implementation.
Figure 8E:
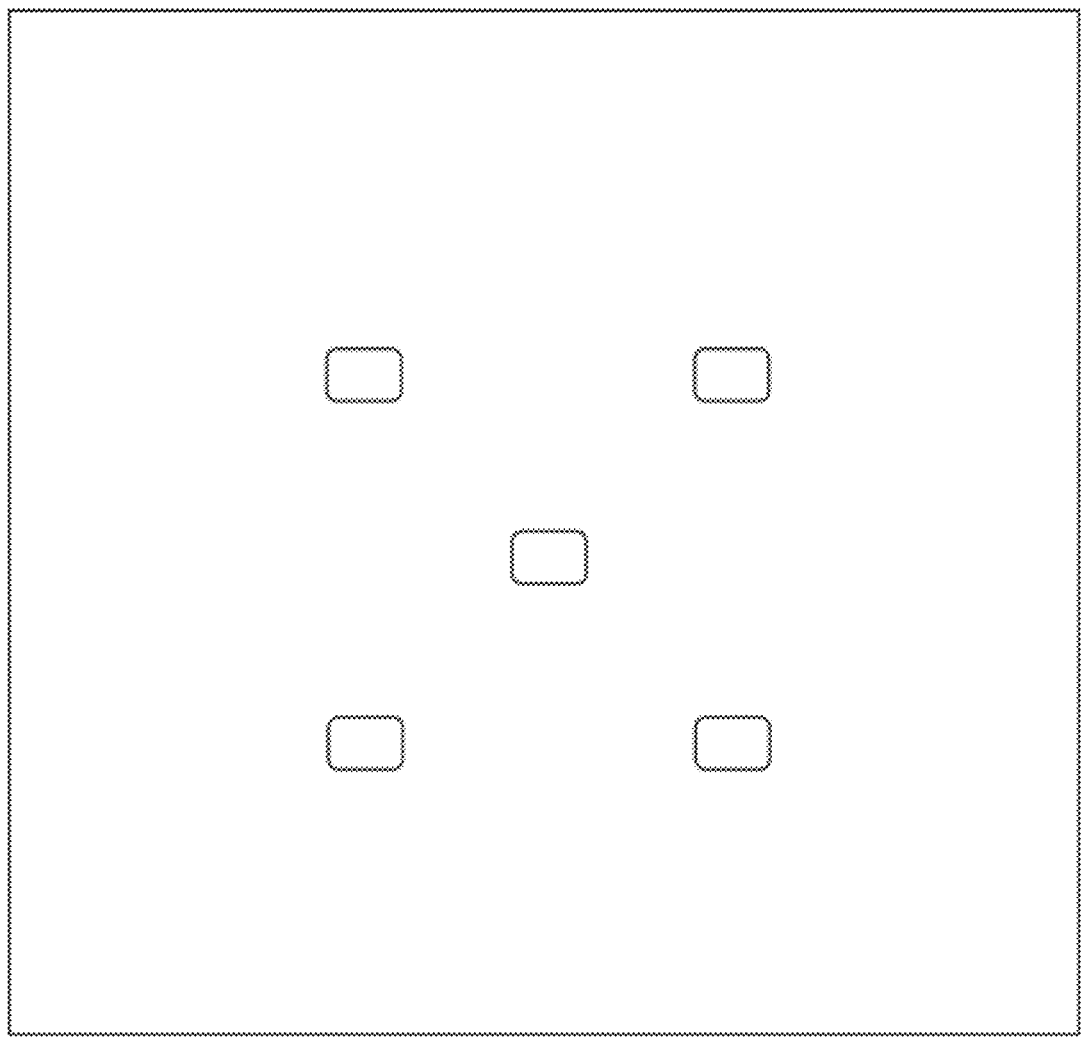
FIG. 8E shows a pinhole mask that covers a cellphone screen, in a cellphone implementation.

In this third prototype, masks comprise 5 pinholes, as shown in FIG. 8E. The central pinhole 801 performs the measurement and peripheral pinholes 802 803, 804, 805 provide reference points. For instance, for a pupil radius of ≈1.5 mm, reference points drawn 5 mm off-center reach the crystallin close to the pupil border and are projected at 0.3 mm from the foveal center.

Figure 8F:
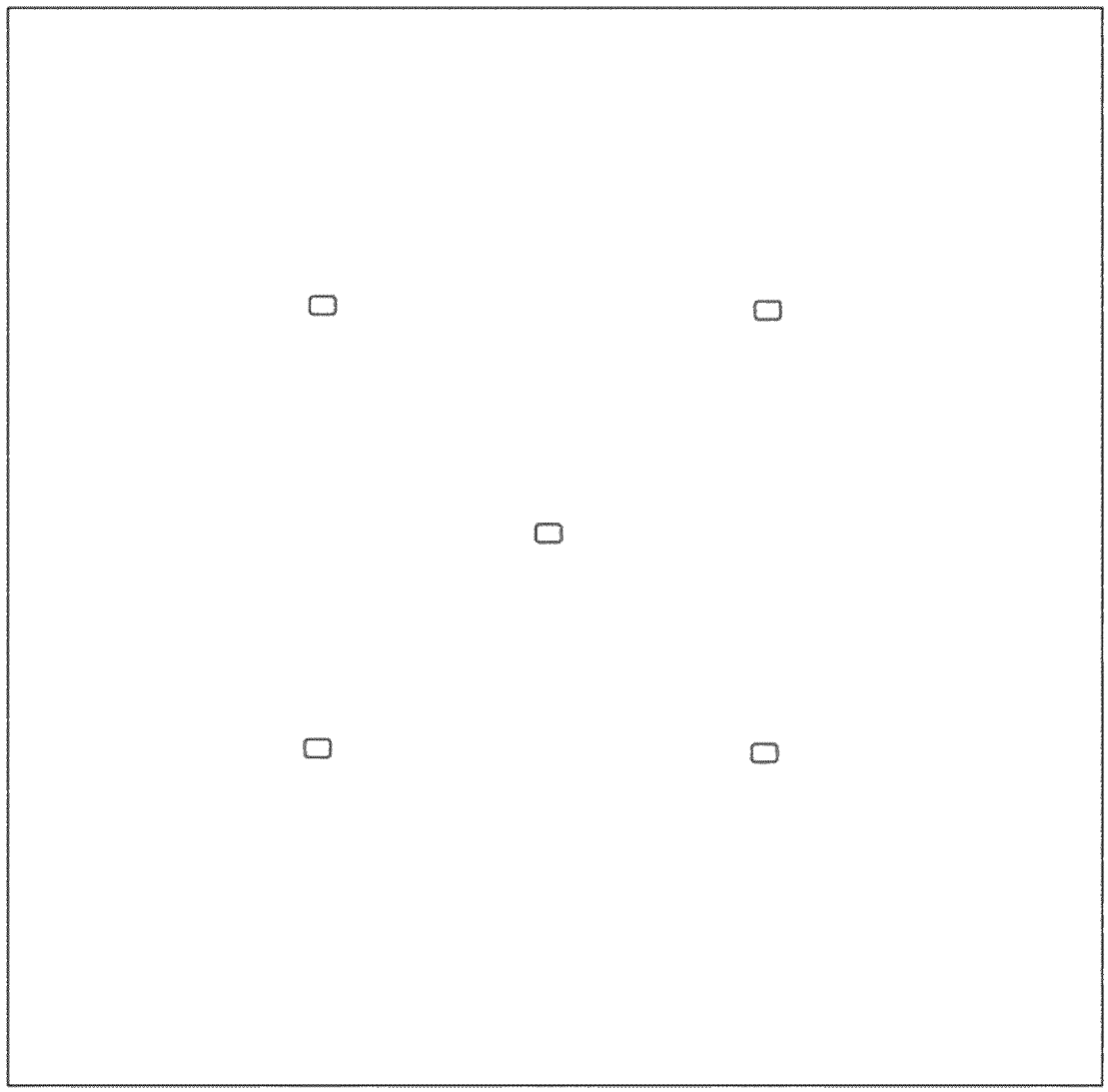
FIG. 8F shows a user's view, in a cellphone implementation.
Figure 8G:
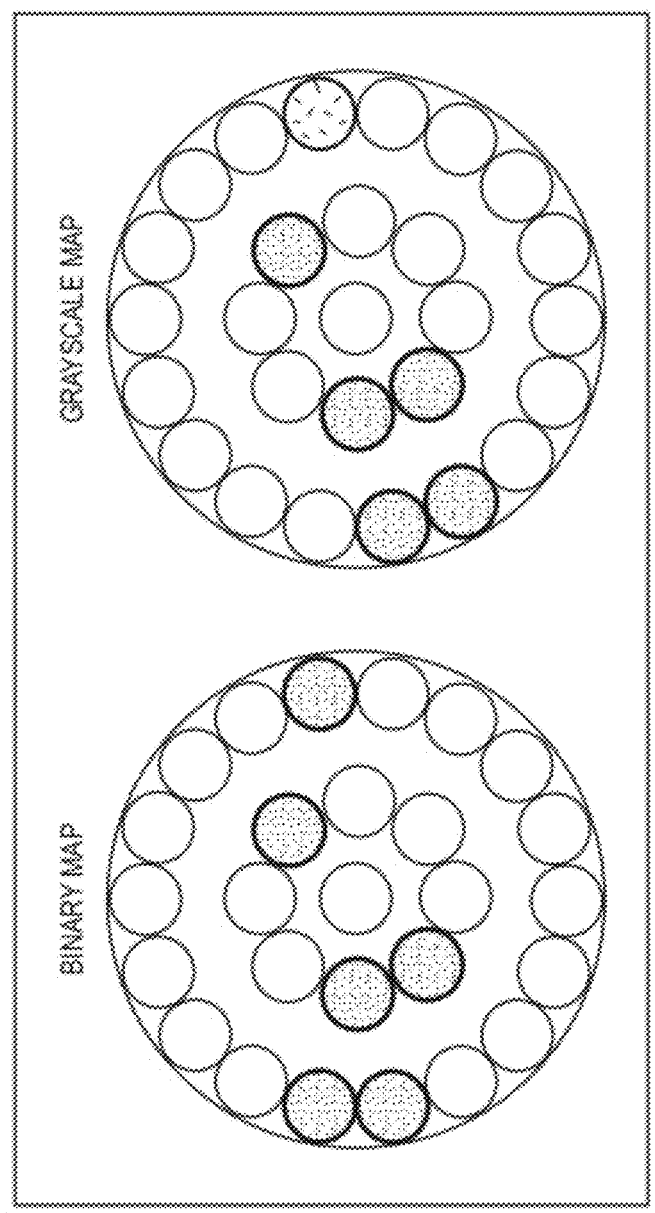
FIG. 8G shows a cell phone screen, displaying opacity and attenuation maps.

FIG. 8D shows a display on a cellphone screen, in a cellphone implementation. The center square is moving and scanning for cataracts while the four in the borders are used as reference points to keep the eye's gaze steady. FIG. 8E shows a pinhole mask that covers a cellphone screen, in a cellphone implementation. FIG. 8F shows a user's view (what the user sees), in a cellphone implementation. FIG. 8G shows a cell phone screen, displaying opacity and attenuation maps.

In each of these three prototypes, an input device 804, 814, 824 accepts input from a human user. The input device may comprise, for example, a keyboard, mouse, graphical user interface, human computer interface, human interface device, touchscreen, light pen, pointing device, pointing stick, microphone, other audio input device, button, switch, potentiometer, trimmer, sensor or transducer, and in each case may further include signal processing devices.

The input that is accepted by the input device may comprise, for example, opacity input, attenuation input, PSF input or contrast input, each as defined below.

In each of these three prototypes, a processor 805, 815, 825 processes data indicative of human input received through the input device, and other data, to calculate cataract maps. The processor may further control the display or operation of the optical apparatus (e.g., comprising dual-stacked LCDs, or a projector or cell phone screen) that delivers light to the crystalline lens. Also, optionally, a processor generates signals for controlling a visual display to render a simulation of what a view would look like as seen by a cataract-affected eye.

The processor may comprise one or more computer processors, at least some of which may be remote from others or from the input device or optical apparatus. The one or more processors may be connected wirelessly, or by wired connection, or by some combination of the wireless and wired connections.

Figure 9A:
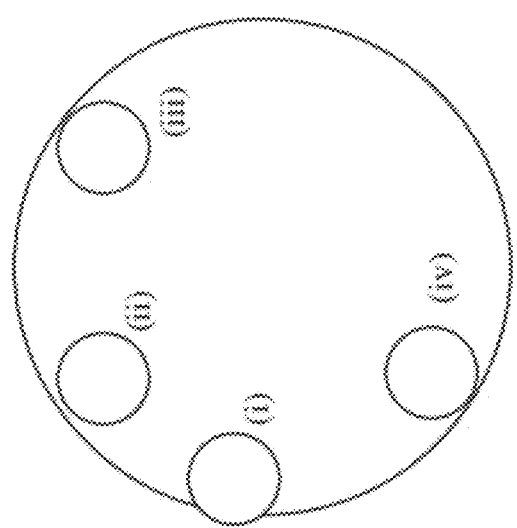
FIG. 9A is a diagram of an eye, in which circles indicate areas with cataracts.
Figure 9B:
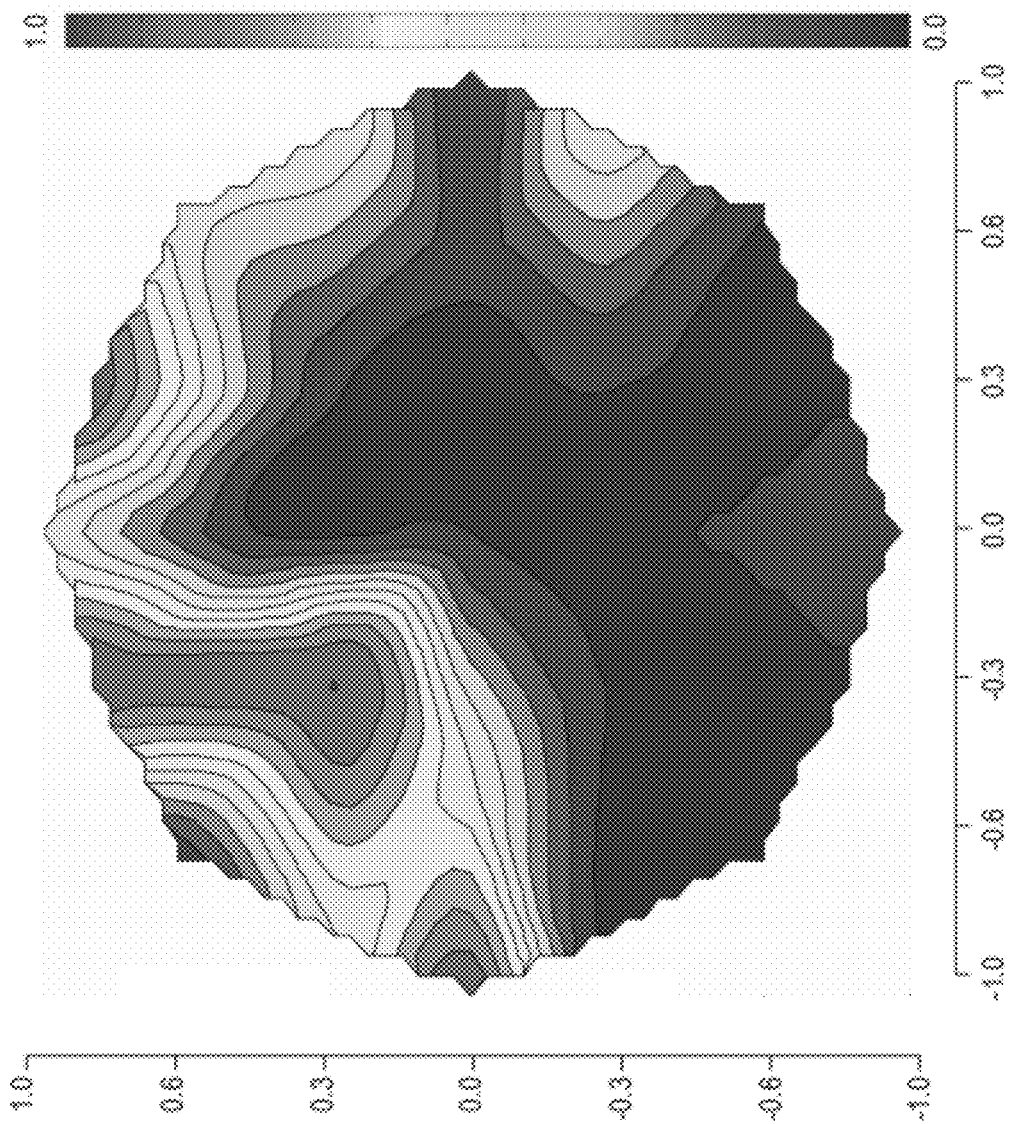
FIGS. 9B and 9C are bilinearly interpolated opacity maps and attenuation maps, respectively, for that eye.
Figure 9C:
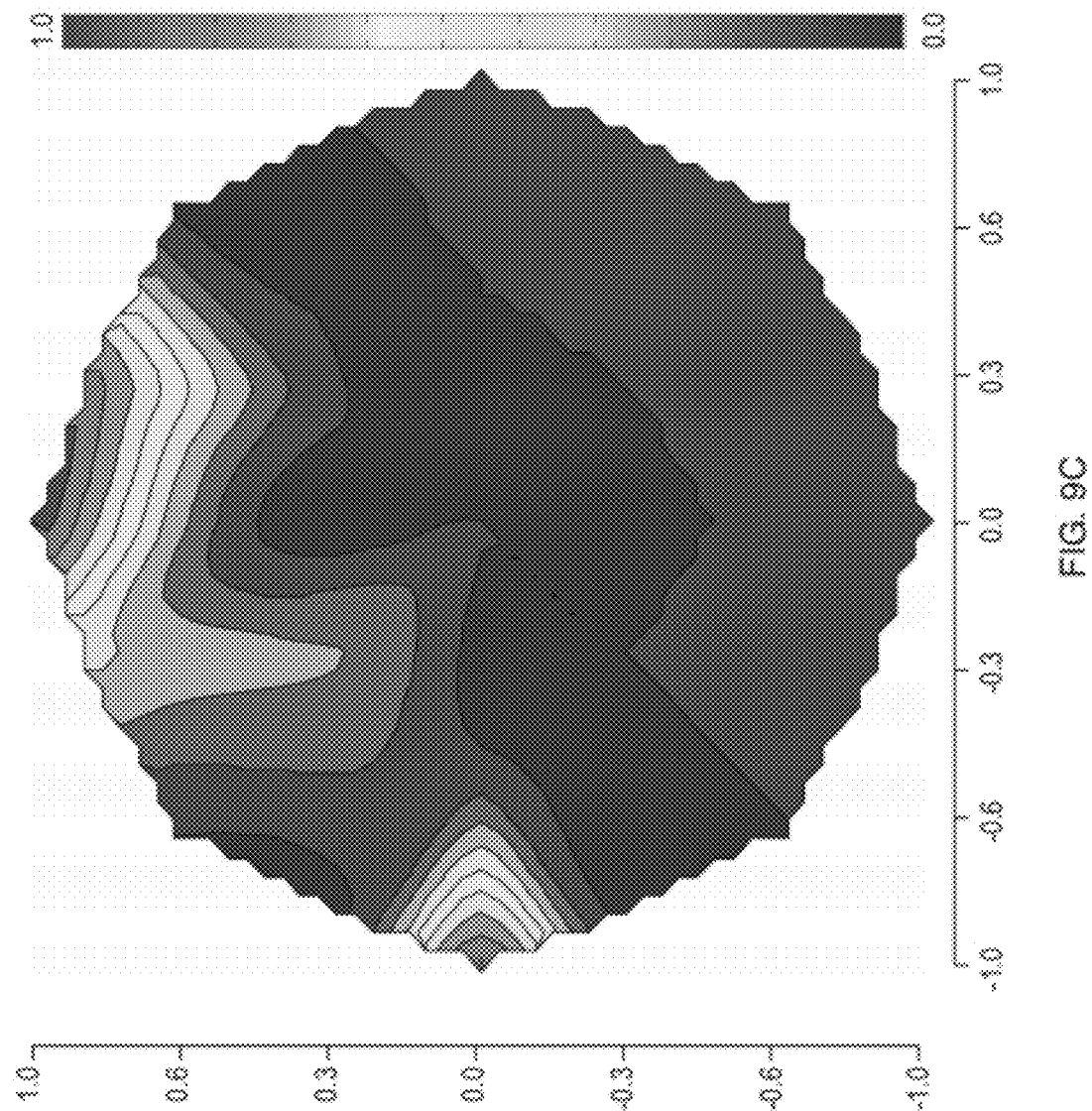

FIG. 9A is a diagram of an eye, in which circles indicate areas with cataracts. FIGS. 9B and 9C are bilinearly interpolated opacity maps and attenuation maps, respectively, for that eye.

DEFINITIONS AND CLARIFICATIONS

Here are a few definitions and clarifications. As used herein:

The terms "a" and "an", when modifying a noun, do not imply that only one of the noun exists.

An "attenuation map" is a map that includes information about how much different regions of a lens attenuate light.

An "attenuation measure" is a value indicating how much a region of a lens attenuates light.

"Attenuation input" is input from a human, which input is used in calculating an attenuation map.

A "cataract map" is a map that includes information about one or more cataracts.

A "cataract region" is a region in the crystalline lens, in which region one or more cataracts are located.

"Contrast input" is input from a human, which input is used in calculating a contrast map.

A "contrast map" of a lens is a map that includes information about sensitivity to visual contrast, depending on the region of the lens through which light travels.

A "contrast measure" for a particular region of a lens is a value indicating sensitivity to visual contrast, for light that travels through that region.

The phrase "for example" means that the one or more examples that follow the phrase are non-limiting examples.

The examples in these definitions and clarifications are not limiting.

In the context of an optical system, "front" is optically closer to a viewer's eye than "rear", and similar terms shall be construed in a like manner. For example, a first element is "behind" a second element in an optical system if the first element is optically further from a viewer's eye than the second element.

The term "include" shall be construed broadly, as if followed by "without limitation".

"Indicate" (and similar terms, such as "indicative of") shall be construed broadly. For example, data L is indicative of fact M if fact M can be directly or indirectly inferred from or computed from (among other things) data L. Also, input is "indicative of" what a human perceives if it is indicative of at least one aspect of what the human perceives.

"LCD" means liquid crystal display.

A "map" is (1) a set of data regarding one or more variables, which variables vary depending on their 1D, 2D or 3D position, or (2) a visual display of such a set of data. A map may, for example, comprise a visual display such as a 1D map, 2D map or 3D map, or a plot, chart or diagram. Or, for example, a map may comprise a set of data from which such a visual display may be generated.

An "opacity map" is a map that includes information about the position of one or more scattering media (e.g. cataracts) in a lens.

"Opacity input" is input from a human, which input is used in calculating an opacity map.

The term "or" is an inclusive disjunctive. For example "A or B" is true if A is true, or B is true, or both A or B are true.

A pinhole may be formed by an actual hole (e.g., in a mask) or by one or more pixels in an electronic visual display (such as an LCD) that attenuate light less than surrounding pixels.

A "point" is illuminated if one or more pixels at or adjacent to that point are illuminated.

A pinhole is "at a point" if the pinhole comprises one or more pixels at or adjacent to that point.

A "processor" means one or more computer processors, at least some of which processors may be spatially remote from other processors.

"PSF" means point spread function.

"PSF input" is input from a human, which input is used in calculating a PSF map.

A "PSF map" is a map that includes data regarding PSFs corresponding to different regions of a lens.

A "sector" or "region" of a lens is an area in a plane, which plane intersects the lens and is normal to the optical axis of the lens.

A "spatial light attenuator" is a device that attenuates light in a spatially-varying way. For example, a "spatial light attenuator" may comprise an LCD or a mask. The pattern of light attenuation may be static or may vary over time, and may comprise a pinhole or other pattern.

A "spatial visual display" is a device that produces a spatially varying optical pattern. For example, a "spatial visual display" may comprise a spatial light attenuator or may comprise a light emitting device such as an LED screen or even a simple flashlight with an additional mask to filter light. The optical pattern produced by a spatial visual display may be static or may vary over time, and may comprise a pinhole or other pattern.

Terms such as "first path", "second path", "first point", "second point", "point W", "point X", "pattern Y", and "pattern Z", are, unless the context clearly indicates otherwise, solely for ease of reference. Such terms do not imply any temporal order or other order, or any shape. For example, a "first path" of light does not necessarily precede in time a "second path" of light. Also, for example, "pattern Z" does not mean a pattern in a shape of a letter Z. However, an "earlier period" occurs earlier in time than another period which it precedes.

A pattern or point may be either static or time-varying, unless the context clearly indicates otherwise.

Variants:

This invention may be implemented in many different ways. Here are a few non-limiting examples:

The scattering or reflecting media being measured is not limited to a human eye, but may instead be a lens (or combination of lenses) in any optical system. For example, the eye can be replaced by a camera, in order (a) to measure aberrations in a camera lens that cause scattering or reflection, and (b) to render (simulate) a scene that approximates the effect of these camera aberrations. In that case, the eye is replaced by a camera and an operator observes what the camera is capturing (e.g., through the viewfinder, live view, or live view where the camera is connected into a computer) and gives feedback using an input device. A processor uses data (e.g., regarding the input and regarding the time-varying path that light travels through the camera lens that is being measured) to compute opacity, attenuation, contrast and point spread function maps for the camera lens. Also, optionally, a processor generates signals for controlling a visual display to render a simulation of what a picture would look like if taken by the same camera.

The renderings and maps are not limited to being in grayscale. For example, they may be in color.

This invention may be implemented as a method of calculating one or more cataract maps, the method comprising: (a) using an optical apparatus to deliver light through the crystalline lens of an eye of a human, the light traveling in a time-varying path from the optical apparatus through the crystalline lens and to the fovea of the eye, which time-varying path passes through different sectors of the crystalline lens at different times, (b) using an input device to accept input indicative of what the human perceives as the path varies, and (c) using a processor to generate control signals for controlling delivery of light to the crystalline lens by the optical apparatus, and to calculate the one or more cataract maps, based at least in part on data indicative of the input and data indicative of the time-varying path.

Furthermore: (1) the optical apparatus may deliver light rays to different positions in the crystalline lens at different times, at angles that cause (or would cause, if the eye had no optical aberrations) all of the light rays in the set to focus on a single identical point in the retina of the eye; (2) at least one of the cataract maps may indicate location of at least one cataract in the crystalline lens; (3) at least one of the cataract maps may indicate how much a region in the crystalline lens attenuates light; (4) at least one of the cataract maps may indicate a point spread function of a region in the crystalline lens; (5) at least one of the cataract maps may indicate a contrast measure for a region in the crystalline lens; (6) the method may further comprise the step of measuring size of the pupil of the eye; (7) the light may be pre-warped to compensate for at least some optical aberrations, other than cataracts, in the eye; and (8) the optical apparatus may comprise a front component and a rear component, the front component being optically closer to the eye than the second component, the front component being a spatial light attenuator and the rear component being a spatial visual display.

Also, (A) during a first period, (i) different points in the rear component may be illuminated, one point at a time, in a sequence, (ii) the front component may display one or more pinholes, and light from each of the different points in the rear component may be focused on the fovea of the eye, and (iii) the input device may receive opacity input indicating that the human perceives a reduction in perceived light intensity at one or more times during the first period, (B) the processor may calculate an opacity map, based at least in part on data indicative of the opacity input and data indicative of the sequence, which opacity map identifies a set of one or more cataract regions in the crystalline lens in which cataracts are located, and (C) the processor may indentify a clear region in the crystalline lens, which clear region attenuates light no more than any other region in the crystalline lens.

Also, (A) during a second period, (i) the rear component may alternate between illuminating a first point on the rear component and a second point on the rear component (thereby defining a first alternating sequence), (ii) the front component may display one or more pinholes, (iii) light that travels on a first path may be attenuated inside the crystalline lens more than light that travels on a second path, (iv) light that travels on the first path may go from the first point through a particular cataract region in the crystalline lens to the fovea (the particular region being a member of the set of cataract regions), (v) light that travels on the second path may go from second point through the clear region of the crystalline lens to the fovea, and (vi) a change in intensity may occur, wherein intensity of illumination at the first point is progressively changed until the input device receives attenuation input indicating that the human perceives no difference in intensity of light from the first point and the second point, and (B) the processor may calculate an attenuation measure for the particular cataract region, based at least in part on data indicative of the attenuation input, data indicative of the first alternating sequence, and data indicative of the change in intensity.

Also, (A) during a third period, (i) the rear component may alternate between illuminating point W on the rear component and point X on the rear component (thereby defining a second alternating sequence of illumination), (ii) the front component may display pattern Y and pattern Z, pattern Y being a pinhole, and pattern Z being defined by function $c(x)=\beta g(\sigma,x)+(1-\beta)p(x)$, where $\beta$ is a scaling factor defined by the attenuation value for the particular region, g is a normalized Gaussian function, $\sigma$ is the standard deviation of the normalized Gaussian function (g), and p is a normalized box function, (ii) at least some light from point W may travel through pattern Y and then through the particular cataract region (where it hits a cataract) and then to the fovea, (iii) at least some light from point X may travel through pattern Z and then through the clear region and then to the fovea, and (iv) a change in standard deviation $\sigma$ may occur, wherein standard deviation $\sigma$ is progressively changed until the input device receives PSF input indicating that the human perceives no difference in light from point W and point X, and (B) the processor may calculate a point spread function for the particular cataract region, based at least in part on data indicative of the PSF input, data indicative of the second alternating sequence, and data indicative of the change in standard deviation.

Also, (A) during a fourth period, (i) a single point on the rear component may be illuminated, (ii) the front component may display a specific pattern, (iii) light from the single point may travel through a specific cataract region of the crystalline lens to the fovea (the specific cataract region being a member of the set of cataract regions), and (iv) a change in contrast may occur in the front component, wherein contrast between the specific pattern and its surroundings is increased until the input device receives contrast input indicating that the human perceives the specific pattern, and (B) the processor may calculate a contrast measure for the specific cataract region, based at least in part on data indicative of the contrast input and data indicative of the change in contrast;

The processor may also calculate attenuation measures for all of the set of cataract regions, point spread functions for a first subset of the set of cataract regions, and contrast measures for a second subset of the set of cataract regions, and the attenuation measures may indicate that the second subset attenuates light more than first subset.

Also, (A) during an earlier period (which precedes the first period), (i) the rear component may display a circle and the front component may display a pinhole, (ii) test light from the circle may be focused (or may, in the absence of any optical aberrations in the eye, be focused) on a single point on the retina of the eye, and (iii) an increase in radius may occur, wherein the radius of the circle is progressively increased until the input device receives size input indicating that the human can no longer see the test light, and (B) the processor may calculate a size of the pupil of the eye, based at least in part on data indicative of the size input and data indicative of the increase in radius.

The eye may have at least one cataract, and the processor may also generate control signals for rendering an image that shows a scene as it would be perceived by the eye without correction for the at least one cataract.

This invention may be implemented as apparatus comprising, in combination: (a) at least one electronic display for delivering light, which light travels through the crystalline lens of an eye of a human to the fovea of the eye in a path that varies over time, which path passes through different sectors of the crystalline lens at different times, and (b) input means for accepting input from the human indicative of what the human perceives as the path varies, and for generating signals (which signals are indicative of the input) for transmission to a processor for use in calculating an opacity map and an attenuation map, respectively, of at least one region of the crystalline lens.

This invention may be implemented as a method comprising, in combination: (a) delivering light through a lens, the light traveling in a time-varying path from a spatial visual display through the lens and to a focal area, which time-varying path passes through different sectors of the lens at different times, (b) using an input device to accept input indicative of images captured at the focal area, and (c) using a processor to generate control signals for controlling delivery of light to the lens by the spatial visual display, and to calculate an opacity map and an attenuation map of the lens, based at least in part on data indicative of the input and data indicative of the time-varying path. Furthermore: (1) the lens may be a camera lens, and (2) the input may be from a human.

CONCLUSION

It is to be understood that the methods and apparatus which have been described above are merely illustrative applications of the principles of the invention. Numerous modifications may be made by those skilled in the art without departing from the scope of the invention. The scope of the invention is not to be limited except by the claims that follow.

What is claimed is:

1. A method comprising:
   (a) using an optical apparatus to deliver light along at least a set of different paths such that during a period of time (i) each path in the set is from the optical apparatus through the crystalline lens of an eye of a human to the fovea of the eye, (ii) at a first time during the period, the light travels on a first path out of the set of paths, entering the crystalline lens at a first entrance point, (iii) at a second time during the period, the light travels on a second path out of the set of paths, entering the crystalline lens at a second entrance point, (iv) the first entrance point is different than the second entrance point, the first path is different than the second path, and the first time is different than the second time, and (v) the light does not travel on the second path at the first time and does not travel on the first path at the second time;
   (b) using an input device to accept input indicative of what the human perceives as the light travels along the different paths; and
   (c) using a processor
      to generate control signals for controlling delivery of light to the crystalline lens by the optical apparatus, and
      to calculate one or more cataract maps, based at least in part on data indicative of the input and data indicative of the paths traveled by the light.

2. The method of claim 1, wherein the different paths terminate, or would terminate if the eye had no optical aberrations, at a single identical point in the retina of the eye.

3. The method of claim 1, wherein at least one of the cataract maps indicates location of at least one cataract in the crystalline lens.

4. The method of claim 1, wherein at least one of the cataract maps indicates how much a region in the crystalline lens attenuates light, which region includes a cataract.

5. The method of claim 1, wherein at least one of the cataract maps indicates a point spread function of a region in the crystalline lens, which region includes a cataract.

6. The method of claim 1, wherein at least one of the cataract maps indicates a contrast measure for a region in the crystalline lens, which region includes a cataract.

7. The method of claim 3, further comprising the step of measuring size of the pupil of the eye.

8. The method of claim 1, wherein the light is pre-warped to compensate for at least some optical aberrations, other than cataracts, in the eye.

9. The method of claim 1, wherein the optical apparatus comprises a front component and a rear component, the front component being optically closer to the eye than the rear component, the front component being a spatial light attenuator and the rear component being a spatial visual display.

10. The method of claim 9, wherein:
   (a) during a first period
      (i) different points in the rear component are illuminated, one point at a time, in a sequence,
      (ii) the front component displays one or more pinholes, light from each of the different points in the rear component is focused on the fovea of the eye, and
      (iii) the input device receives opacity input indicating that the human perceives a reduction in perceived light intensity at one or more times during the first period,
   (b) the processor calculates an opacity map, based at least in part on data indicative of the opacity input and data indicative of the sequence, which opacity map identifies a set of one or more cataract regions in the crystalline lens in which cataracts are located, and (c) the processor identifies a clear region in the crystalline lens, which clear region attenuates light no more than any other region in the crystalline lens.

11. The method of claim 10, wherein:
(a) during a second period,
  (i) the rear component alternates between illuminating a first point on the rear component and a second point on the rear component, thereby defining a first alternating sequence,
  (ii) the front component displays one or more pinholes,
  (iii) light that travels on a first path is attenuated inside the crystalline lens more than light that travels on a second path,
  (iv) light that travels on the first path goes from the first point through a particular cataract region in the crystalline lens to the fovea, the particular region being a member of the set of cataract regions,
  (v) light that travels on the second path goes from second point through the clear region of the crystalline lens to the fovea, and
  (vi) a change in intensity occurs, wherein intensity of illumination at the first point is progressively changed until the input device receives attenuation input indicating that the human perceives no difference in intensity of light from the first point and the second point, and
(b) the processor calculates an attenuation measure for the particular cataract region, based at least in part on data indicative of the attenuation input, data indicative of the first alternating sequence, and data indicative of the change in intensity.

12. The method of claim 11, wherein:
(a) during a third period,
  (i) the rear component alternates between illuminating point W on the rear component and point X on the rear component, thereby defining a second alternating sequence of illumination,
  (ii) the front component displays pattern Y and pattern Z, pattern Y being a pinhole, and pattern Z being defined by function $c(x)=\beta g(\sigma,x)+(1-\beta)p(x)$, where $\beta$ is a scaling factor defined by the attenuation value for the particular region, g is a normalized Gaussian function, $\sigma$ is the standard deviation of the normalized Gaussian function (g), and p is a normalized box function,
  (iii) at least some light from point W travels through pattern Y and then through the particular cataract region where it hits a cataract and then to the fovea,
  (iv) at least some light from point X travels through pattern Z and then through the clear region and then to the fovea, and
  (v) a change in standard deviation $\sigma$ occurs, wherein standard deviation $\sigma$ is progressively changed until the input device receives PSF input indicating that the human perceives no difference in light from point W and point X, and
(b) the processor calculates a point spread function for the particular cataract region, based at least in part on data indicative of the PSF input, data indicative of the second alternating sequence, and data indicative of the change in standard deviation.

13. The method of claim 11, wherein:
(a) during a specific period,
  (i) a single point on the rear component is illuminated,
  (ii) the front component displays a specific pattern,
  (iii) light from the single point travels through a specific cataract region of the crystalline lens to the fovea, the specific cataract region being a member of the set of cataract regions, and
  (iv) a change in contrast occurs in the front component, wherein contrast between the specific pattern and its surroundings is increased until the input device receives contrast input indicating that the human perceives the specific pattern, and
(b) the processor calculates a contrast measure for the specific cataract region, based at least in part on data indicative of the contrast input and data indicative of the change in contrast.

14. The method of claim 10, wherein the processor also calculates attenuation measures for all of the set of cataract regions, point spread functions for a first subset of the set of cataract regions, and contrast measures for a second subset of the set of cataract regions, and the attenuation measures indicate that the second subset attenuates light more than first subset.

15. The method of claim 10, wherein:
(a) during an earlier period which precedes the first period,
  (i) the rear component displays a circle and the front component displays a pinhole,
  (ii) test light from the circle is focused, or would in the absence of any optical aberrations in the eye be focused, on a single point on the retina of the eye, and
  (iii) an increase in radius occurs, wherein the radius of the circle is progressively increased until the input device receives size input indicating that the human can no longer see the test light, and
(b) the processor calculates a size of the pupil of the eye, based at least in part on data indicative of the size input and data indicative of the increase in radius.

16. The method of claim 12, wherein the eye has at least one cataract, and the processor also generates control signals for rendering an image that shows a scene as it would be perceived by the eye without correction for the at least one cataract.

17. A system comprising, in combination:
(a) apparatus for delivering light along at least a set of different paths such that during a period of time (i) each path in the set is from the optical apparatus through the crystalline lens of an eye of a human to the fovea of the eye, (ii) at a first time during the period, the light travels on a first path out of the set of paths, entering the crystalline lens at a first entrance point, (iii) at a second time during the period, the light travels on a second path out of the set of paths, entering the crystalline lens at a second entrance point, (iv) the first entrance point is different than the second entrance point, the first path is different than the second path, and the first time is different than the second time, and (v) the light does not travel on the second path at the first time and does not travel on the first path at the second time; and
(b) input means for accepting input from the human indicative of what the human perceives as the travels along the different paths, and for generating signals that are indicative of the input and that are for transmission to a processor for use in calculating an opacity map and an attenuation map, respectively, of at least one region of the crystalline lens.

18. A method comprising, in combination:
(a) delivering light through a camera lens, the light traveling along a set of paths from a spatial visual display through the lens and to a focal area, such that the light travels on different paths in the set at different times and such that different paths in the set pass through different sectors of the lens,
(b) using an input device to accept input from a human indicative of images captured at the focal area, and
(c) using a processor
  (i) to generate control signals for controlling delivery of light to the lens by the spatial visual display, and
  (ii) to calculate an opacity map and an attenuation map of the lens, based at least in part on data indicative of the input and data indicative of the paths traveled by the light at different times.

19. A method comprising:
(a) using an optical apparatus to deliver light along at least a set of different paths at different times, such that (i) each path in the set is from the optical apparatus through the crystalline lens of an eye of a human and to the fovea of the eye, and (ii) different paths in the set enter the crystalline lens at different entrance points,
(b) using an input device to accept input indicative of what the human perceives as the light travels along different paths in the set; and
(c) using a processor
  to generate control signals for controlling delivery of light to the crystalline lens by the optical apparatus, and
  to calculate one or more cataract maps, based at least in part on data indicative of the input and data indicative of the paths traveled by the light at different times;
wherein
  (i) the optical apparatus comprises a front component and a rear component,
  (ii) the front component is optically closer to the eye than the rear component,
  (iii) the front component comprises a spatial light attenuator and the rear component comprises a spatial visual display.

20. The method of claim 19, wherein:
(a) each pixel in the rear component maps to a region on the crystalline lens; and
(b) each pixel in the front component maps to a retinal position.

* * * * *